(12) United States Patent
Peng et al.

(10) Patent No.: US 12,334,498 B2
(45) Date of Patent: Jun. 17, 2025

(54) ELECTROLYTE, ELECTROCHEMICAL DEVICE, AND ELECTRONIC DEVICE

(71) Applicant: Ningde Amperex Technology Limited, Fujian (CN)

(72) Inventors: Xiexue Peng, Fujian (CN); Jianming Zheng, Fujian (CN); Chao Tang, Fujian (CN)

(73) Assignee: NINGDE AMPEREX TECHNOLOGY LIMITED, Ningde (CN)

( * ) Notice: Subject to any disclaimer, the term of this patent is extended or adjusted under 35 U.S.C. 154(b) by 511 days.

(21) Appl. No.: 17/708,617

(22) Filed: Mar. 30, 2022

(65) Prior Publication Data
US 2022/0223914 A1 Jul. 14, 2022

Related U.S. Application Data

(63) Continuation of application No. PCT/CN2020/138741, filed on Dec. 23, 2020.

(51) Int. Cl.
*H01M 10/0567* (2010.01)

(52) U.S. Cl.
CPC ......... *H01M 10/0567* (2013.01); *H01M 2300/0025* (2013.01)

(58) Field of Classification Search
CPC ......... H01M 10/0525; H01M 10/0567; H01M 10/4235; H01M 2300/0025; Y02E 60/10
See application file for complete search history.

(56) References Cited

U.S. PATENT DOCUMENTS

| | | | |
|---|---|---|---|
| 3,148,206 A | 9/1964 | Rauhut et al. | |
| 3,284,543 A | 11/1966 | Gillham et al. | |
| 2010/0297508 A1 | 11/2010 | Lee et al. | |
| 2017/0077552 A1* | 3/2017 | Taeda | H01G 11/64 |
| 2018/0269528 A1* | 9/2018 | Zhang | H01M 4/131 |
| 2020/0144672 A1 | 5/2020 | Ji et al. | |
| 2022/0123363 A1* | 4/2022 | Li | H01M 10/0525 |

FOREIGN PATENT DOCUMENTS

| | | | | |
|---|---|---|---|---|
| CN | 1667864 | A | 9/2005 | |
| CN | 105958120 | A | 9/2016 | |
| CN | 106848381 | A | 6/2017 | |
| CN | 109065951 | A | 12/2018 | |
| CN | 106415910 | B | 5/2019 | |
| CN | 109786834 | A | 5/2019 | |
| CN | 109786835 | A * | 5/2019 | ........ H01M 10/0525 |
| CN | 111628219 | A | 9/2020 | |
| CN | 111740165 | A | 10/2020 | |
| CN | 111987359 | A | 11/2020 | |
| FR | 1333818 | A | 8/1963 | |
| GB | 923532 | A | 4/1963 | |
| JP | 2006294332 | A | 10/2006 | |
| JP | 201337993 | A | 2/2013 | |
| JP | 2016536776 | A | 11/2016 | |
| WO | 2015075811 | A1 | 5/2015 | |
| WO | 2020092267 | A1 | 5/2020 | |
| WO | 2020151658 | A1 | 7/2020 | |

OTHER PUBLICATIONS

International Search Report issued on Sep. 10, 2021 in corresponding International Patent Application No. PCT/CN2020/138741; 4 pages.

Notification of Grant of Invention Patent Rights issued on Jan. 11, 2023, in corresponding Chinese Application No. 202080040377.3, 8 pages.

Office Action issued on May 30, 2022, in corresponding Chinese Application No. 202080040377.3, 18 pages.

(Continued)

*Primary Examiner* — Victoria H Lynch
(74) *Attorney, Agent, or Firm* — Maier & Maier, PLLC

(57) ABSTRACT

An electrolyte includes a compound represented by formula I-A, where $A^1$, $A^2$, and $A^3$ are each independently selected from formula I-B or formula I-C, and at least two of $A^1$, $A^2$, and $A^3$ are formula I-C. In formula I-A, n is selected from integers 1 to 10, and m is selected from 0 or 1. In formula I-B and formula I-C, ⌇— represents a site at which two adjacent atoms are joined. The electrolyte can significantly improve high-temperature storage performance, cycle performance, and floating charge performance of the electrochemical device.

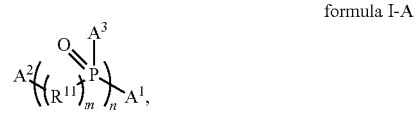

formula I-A

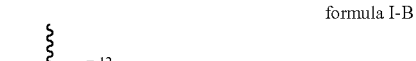

formula I-B

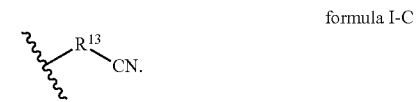

formula I-C

16 Claims, No Drawings

(56) References Cited

OTHER PUBLICATIONS

Office Action issued on Oct. 10, 2023, in corresponding Japanese Application No. 2021-533327, 6 pages.
Office Action issued on Apr. 25, 2023, in corresponding Japanese Application No. 2021-533327, 6 pages.
Notice of Allowance issued on Oct. 4, 2023, in corresponding Korean Application No. 10-2021-7017761, 4 pages.
Office Action issued on Apr. 3, 2023, in corresponding Korean Application No. 10-2021-7017761, 11 pages.
Extended European Search Report issued on Nov. 30, 2022, in corresponding European Application No. 20953503.8, 10 pages.

\* cited by examiner

ELECTROLYTE, ELECTROCHEMICAL DEVICE, AND ELECTRONIC DEVICE

CROSS REFERENCE TO RELATED APPLICATIONS

This application is a bypass continuation application of PCT international application: PCT/CN2020/138741 filed on Dec. 23, 2020, the disclosure of which is hereby incorporated by reference in its entirety.

TECHNICAL FIELD

This application relates to the electrochemical field, and specifically, to an electrolyte, an electrochemical device, and an electronic device.

BACKGROUND

Electrochemical devices (for example, lithium-ion batteries) have received widespread attention due to their high energy density, high power density, and stable service life, and therefore been widely used. With the rapid development of technologies, the diversity of market demand, and the rise of energy storage systems and electric vehicle industries in the next few years, people have put forward more requirements on lithium-ion batteries, for example, being thinner, lighter, and having more diverse shapes, higher safety, and higher energy density.

SUMMARY

In some embodiments, this application provides an electrolyte, including a compound represented by formula I-A;

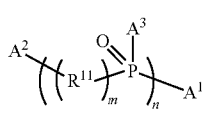

formula I-A where $A^1$, $A^2$, and $A^3$ are each independently selected from formula I-B or formula I-C, and at least two of $A^1$, $A^2$, and $A^3$ are formula I-C;

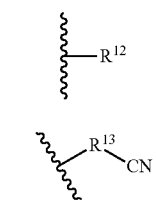

formula I-B formula I-C where in formula I-A, n is selected from integers 1 to 10, and m is selected from 0 or 1; and in formula I-B and formula I-C, $\xi$– represents a site at which two adjacent atoms are joined; $R^{11}$ and $R^{13}$ are each independently selected from substituted or unsubstituted $C_1$-$C_{10}$ alkylene groups, substituted or unsubstituted $C_2$-$C_{10}$ alkenylene groups, substituted or unsubstituted $C_2$-$C_{10}$ alkynylene groups, substituted or unsubstituted $C_3$-$C_{10}$ allenylene groups, substituted or unsubstituted $C_6$-$C_{10}$ arylene groups, or substituted or unsubstituted $C_3$-$C_{10}$ alicyclic hydrocarbon groups, and when substituted, a substituent group includes a halogen; and $R^{12}$ is independently selected from halogens, substituted or unsubstituted $C_1$-$C_{10}$ alkyl groups, substituted or unsubstituted $C_2$-$C_{10}$ alkenyl groups, substituted or unsubstituted $C_2$-$C_{10}$ alkynyl groups, substituted or unsubstituted $C_3$-$C_{10}$ cumulative diene groups, substituted or unsubstituted $C_6$-$C_{10}$ aryl groups, or substituted or unsubstituted $C_3$-$C_{10}$ alicyclic hydrocarbon groups, and when substituted, a substituent group includes a halogen.

In some embodiments, the compound represented by formula I-A includes at least one of compounds represented by formula (I-1) to formula (I-30):

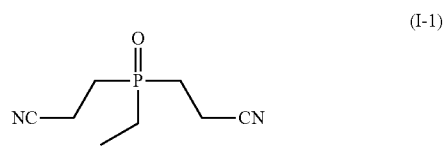

(I-1)

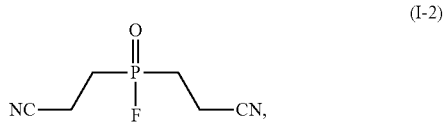

(I-2)

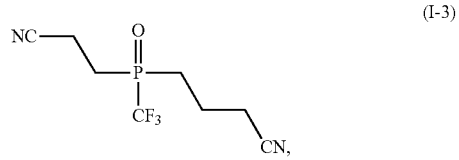

(I-3)

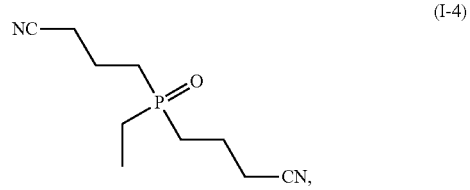

(I-4)

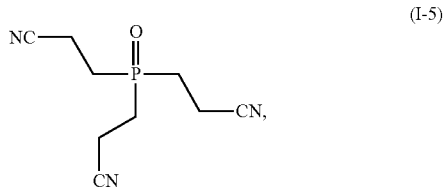

(I-5)

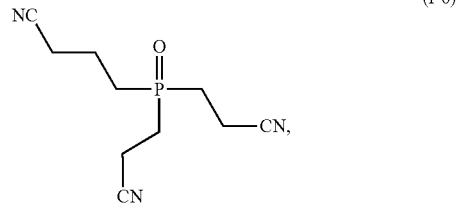

(I-6)

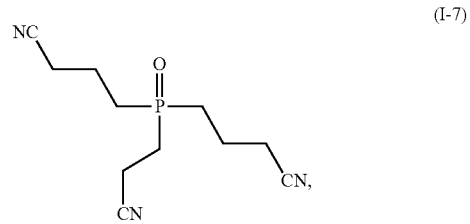

(I-7)

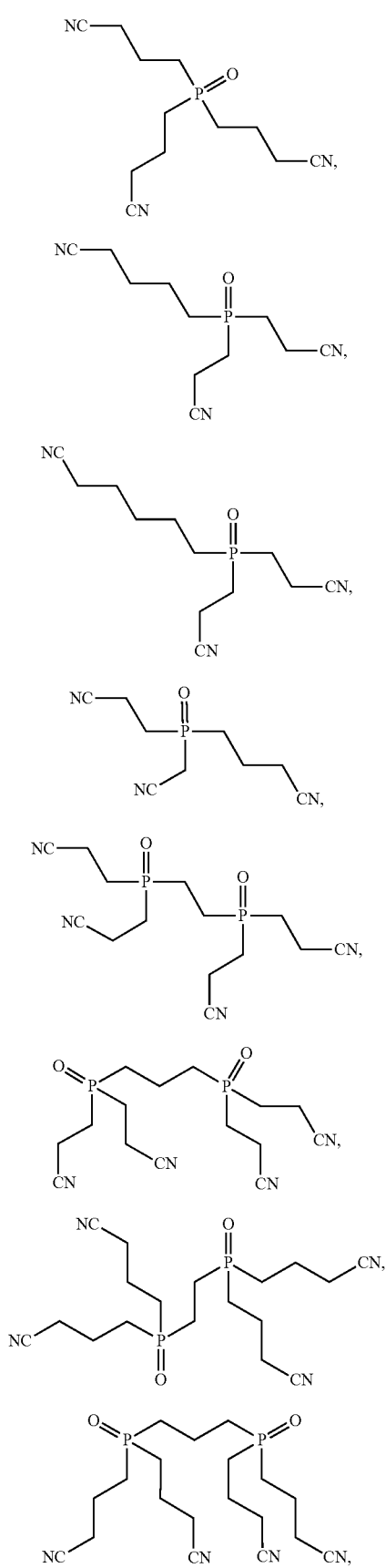
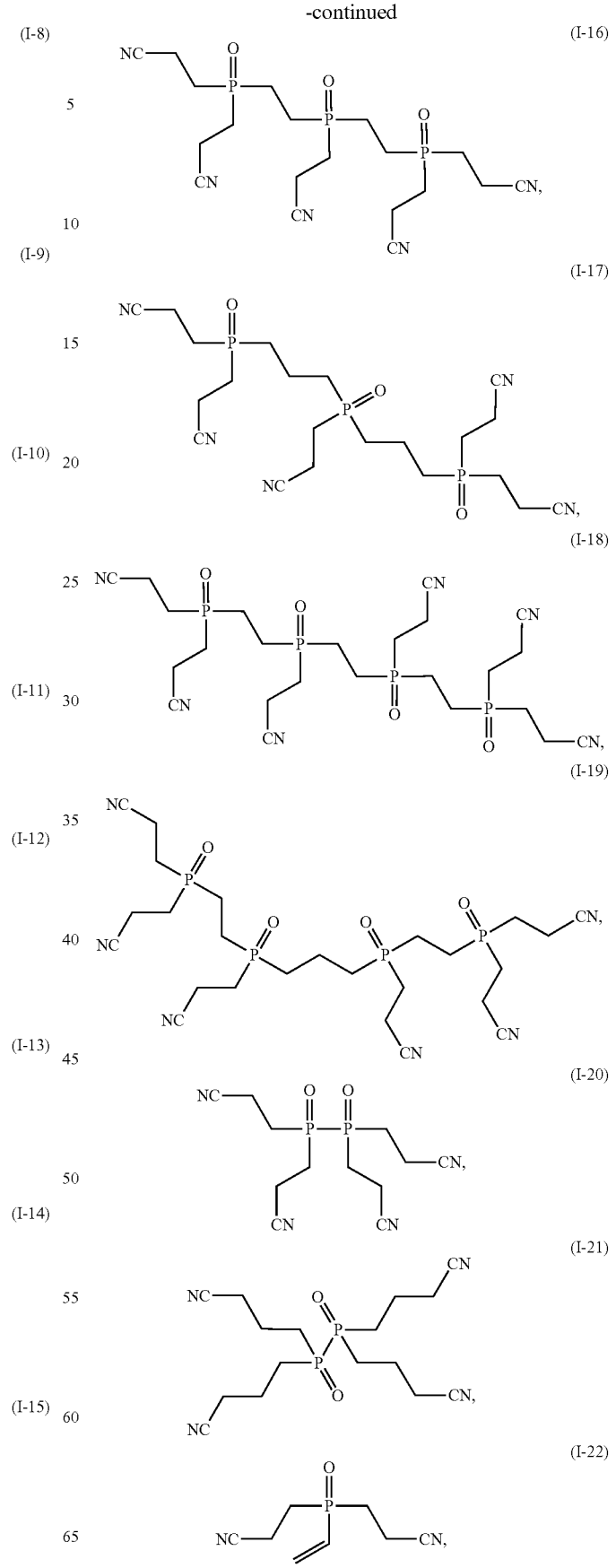

(I-23)
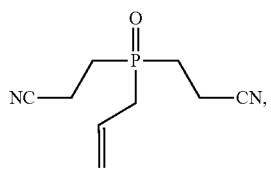

(I-24)
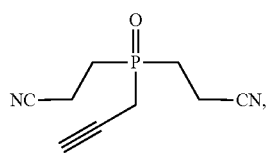

(I-25)
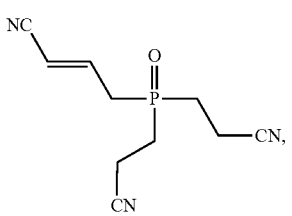

(I-26)
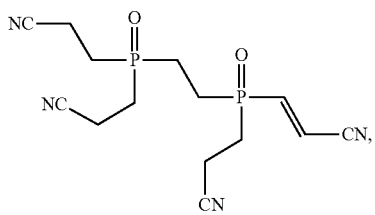

(I-27)
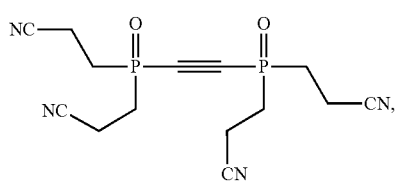

(I-28)
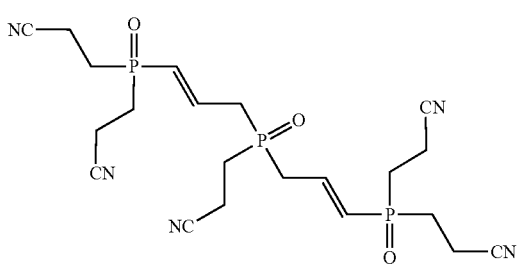

(I-29) and
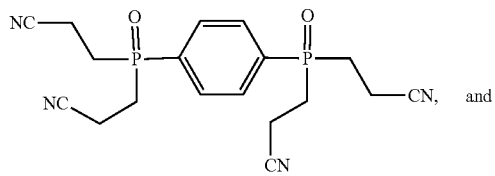

(I-30)
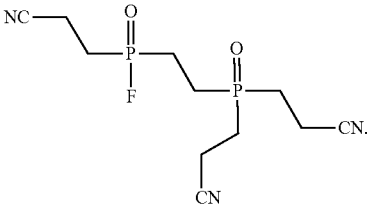

In some embodiments, the compound represented by formula I-A is 0.01% to 10% of the electrolyte by mass.

In some embodiments, the electrolyte further includes at least one of a compound represented by formula II-A, a compound represented by formula III-A, a compound represented by formula IV-A, a compound represented by formula V-A, a compound represented by formula V-B, or a multi-nitrile compound;

formula II-A
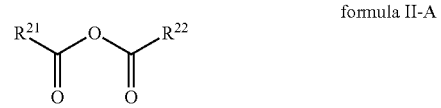

where $R^{21}$ and $R^{22}$ are each independently selected from substituted or unsubstituted $C_1$-$C_5$ alkyl groups, substituted or unsubstituted $C_2$-$C_5$ alkenyl groups, or substituted or unsubstituted $C_2$-$C_5$ alkynyl groups, and when substituted, a substituent group includes a halogen; and $R^{21}$ and $R^{22}$ are capable of being bonded to form a cyclic structure;

formula III-A
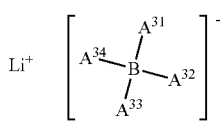

where $A^{31}$, $A^{32}$, $A^{33}$, and $A^{34}$ are each independently selected from one of halogens, formula III-X, formula III-Y, and formula III-Z, and when formula III-Y is selected, two or four of $A^{31}$, $A^{32}$, $A^{33}$, and $A^{34}$ are selected from formula III-Y to form a cyclic structure;

formula III-X

formula III-Y
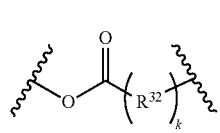

formula III-Z
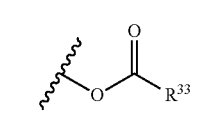

where $R^{31}$ and $R^{33}$ are each independently selected from substituted or unsubstituted $C_1$-$C_6$ alkyl groups, or substituted or unsubstituted $C_2$-$C_6$ alkenyl groups; $R^{32}$ is independently selected from substituted or unsubstituted $C_1$-$C_6$ alkylene groups, or substituted or unsubstituted $C_2$-$C_6$ alkenylene groups; when substituted, a substituent group includes a halogen; represents a site at which two adjacent atoms are joined; and in formula III-Y, an O atom is connected to a B atom in formula III-A, and k is 0 or 1;

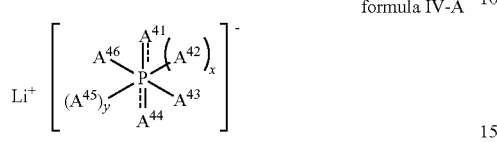

formula IV-A where | represents a single bond or a double bond, and x and y each independently represent 0 or 1; when one || in formula IV-A represents a single bond, one of x and y is 1, and the other of x and y is 0; when two | in formula IV-A both represent a single bond, both x and y are 1; when two | in formula IV-A both represent a double bond, both x and y are 0; $A^{42}$, $A^{43}$, $A^{45}$, and $A^{46}$ are each independently selected from halogens, substituted or unsubstituted $C_1$-$C_6$ alkyl groups, formula IV-B, formula IV-C, and formula IV-D, and when formula IV-C is selected, two or four of $A^{42}$, $A^{43}$, $A^{45}$, and $A^{46}$ are selected from formula IV-C to form a cyclic structure; $A^{41}$ and $A^{44}$ are each independently selected from oxygen, halogens, substituted or unsubstituted $C_1$-$C_6$ alkyl groups, formula IV-B, formula IV-C, or formula IV-D, and when formula IV-C is selected, $A^{41}$ and $A^{44}$ both are formula IV-C to form a cyclic structure; where when substituted, a substituent group includes a halogen; and $A^{41}$, $A^{42}$, $A^{43}$, $A^{44}$, $A^{45}$, and $A^{46}$ are not all fluorine;

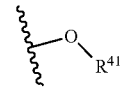

formula IV-B

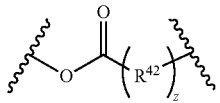

formula IV-C

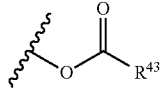

formula IV-D in formula IV-B, formula IV-C, and formula IV-D, $R^{41}$ and $R^{43}$ are each independently selected from substituted or unsubstituted $C_1$-$C_6$ alkyl groups, or substituted or unsubstituted $C_2$-$C_6$ alkenyl groups; and $R^{42}$ is selected from substituted or unsubstituted $C_1$-$C_6$ alkylene groups, or substituted or unsubstituted $C_2$-$C_6$ alkenylene groups; where when substituted, a substituent group includes a halogen; and in formula IV-C, an O atom is connected to a P atom in formula IV-A, and z represents 0 or 1;

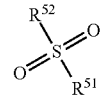

formula V-A

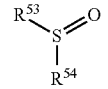

formula V-B where $R^{51}$, $R^{52}$, $R^{53}$, and $R^{54}$ are each independently selected from substituted or unsubstituted $C_1$-$C_5$ alkyl groups, substituted or unsubstituted $C_2$-$C_{10}$ alkenyl groups, substituted or unsubstituted $C_2$-$C_{10}$ alkynyl groups, substituted or unsubstituted $C_3$-$C_{10}$ alicyclic groups, substituted or unsubstituted $C_6$-$C_{10}$ aryl groups, substituted or unsubstituted $C_1$-$C_6$ alicyclic heterocyclic groups, substituted or unsubstituted $C_1$-$C_6$ aromatic heterocyclic groups, or substituted or unsubstituted $C_1$-$C_6$ heteroatom-containing functional groups, where when substituted, a substituent group includes a halogen; $R^{51}$ and $R^{52}$ are capable of being bonded to each other to form a cyclic structure; $R^{53}$ and $R^{54}$ are capable of being bonded to each other to form a cyclic structure; and a heteroatom in the heteroatom-containing functional group includes at least one of B, N, O, Si, P, and S.

In some embodiments, the electrolyte satisfies at least one of the following conditions: (a) the compound represented by formula II-A is 0.01% to 10% of the electrolyte by mass; (b) the compound represented by formula III-A is 0.1% to 5% of the electrolyte by mass; (c) the compound represented by formula IV-A is 0.1% to 5% of the electrolyte by mass; (d) a sum of the compounds represented by formula V-A and formula V-B is 0.01% to 10% of the electrolyte by mass; and (e) the multi-nitrile compound is 0.1% to 10% of the electrolyte by mass.

In some embodiments, the compound represented by formula II-A includes at least one of compounds represented by formula (II-1) to formula (II-22):

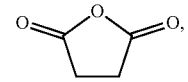

(II-1)

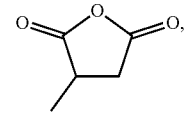

(II-2)

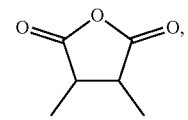

(II-3)

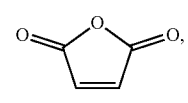

(II-4)

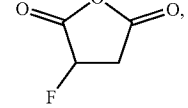

(II-5)

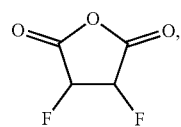 (II-6)

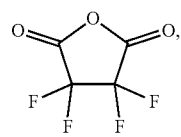 (II-7)

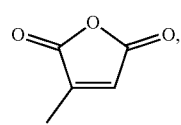 (II-8)

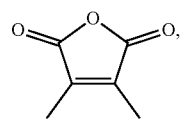 (II-9)

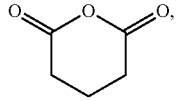 (II-10)

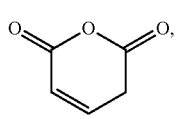 (II-11)

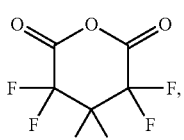 (II-12)

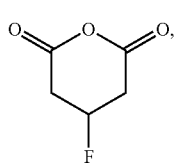 (II-13)

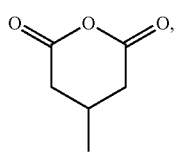 (II-14)

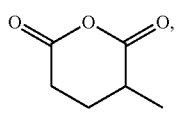 (II-15)

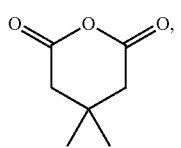 (II-16)

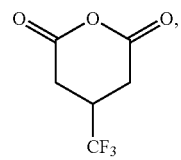 (II-17)

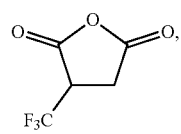 (II-18)

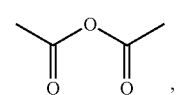 (II-19)

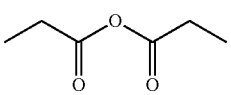 (II-20)

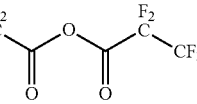 (II-21)

and

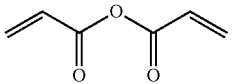 (II-22)

.

In some embodiments, the compound represented by formula III-A includes at least one of lithium tetrafluoroborate, lithium bis(oxalate)borate, and lithium difluoro(oxalato)borate.

In some embodiments, the compound represented by formula IV-A includes at least one of lithium difluorophosphate, lithium difluorobis(oxalato)phosphate, and lithium tetrafluoro(oxalato)phosphate.

In some embodiments, the compound represented by formula V-A includes at least one of compounds represented by formula (V-1) to formula (V-16):

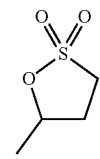 (V-1)

,

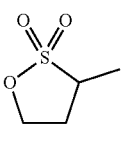 (V-2)

,

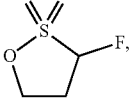 (V-3)

,

-continued

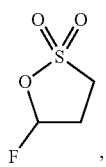 (V-4)

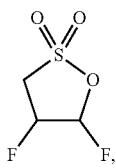 (V-5)

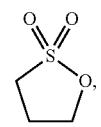 (V-6)

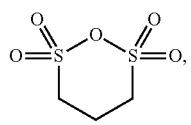 (V-7)

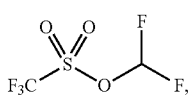 (V-8)

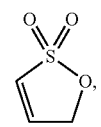 (V-9)

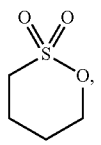 (V-10)

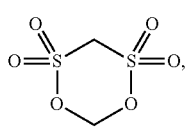 (V-11)

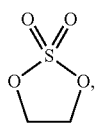 (V-12)

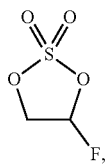 (V-13)

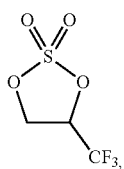 (V-14)

-continued

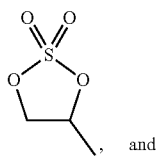 (V-15)

and

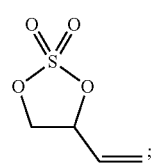 (V-16)

;

and the compound represented by formula V-B includes at least one of compounds represented by formula (V-17) to formula (V-20):

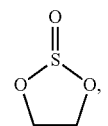 (V-17)

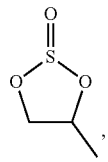 (V-18)

,

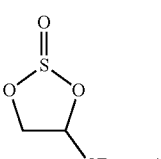 (V-19)

and

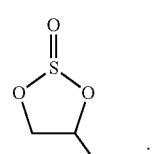 (V-20)

.

In some embodiments, the multi-nitrile compound includes at least one of 1,2,3-tris(2-cyanoethoxy)propane, 1,3,6-hexanetricarbonitrile, 1,2-bis(2-cyanoethoxy)ethane, and adiponitrile.

In some embodiments, this application further provides an electrochemical device, including a positive electrode plate, a negative electrode plate, a separator, and the electrolyte of this application.

In some embodiments, this application further provides an electronic device, including the electrochemical device of this application.

The electrolyte of this application can significantly improve high-temperature storage performance, cycle performance, and floating charge performance of the electrochemical device using the electrolyte.

DETAILED DESCRIPTION

It should be understood that the disclosed embodiments are merely examples of this application and this application can be implemented in various forms. Therefore, specific details disclosed herein should not be construed as a limitation. Instead, they should serve only as a basis for the claims and as an illustrative basis to instruct persons of ordinary skill in the art to implement this application in various ways.

In the descriptions of this application, unless otherwise expressly specified and defined, the terms "additive A", "additive B", "additive C", "additive D", "additive E", "additive F", and the like are only used for illustrative purposes, and cannot be understood as indicating or implying relative importance and mutual relationship. In the descriptions of this application, unless otherwise expressly specified and defined, the letters and numbers in the terms "formula I-A", "formula I-B", "formula I-1", "formula II-A", and "formula II-B", "formula II-1", and the like are only used for marking purposes, and cannot be understood as indicating or implying relative importance, mutual relationship, or chemical elements.

In the description of this application, unless otherwise specified, the functional groups of all compounds may be substituted or unsubstituted.

In the descriptions of this application, unless otherwise specified, the term "heteroatom" refers to an atom other than a C atom and an H atom. In some embodiments, the heteroatom includes at least one of B, N, O, Si, P, and S. In the descriptions of this application, the term "heteroatom-containing functional group" refers to a functional group containing at least one heteroatom. In the descriptions of this application, the term "heterocyclic group" refers to a cyclic group containing at least one heteroatom. In some embodiments, the heterocyclic group includes at least one of an aliphatic heterocyclic group and an aromatic heterocyclic group.

In the descriptions of this application, the term "alicyclic hydrocarbon group" refers to a ring-shaped hydrocarbon with an aliphatic property, with a molecule containing a closed carbocyclic ring.

In the descriptions of this application, an alkylene group is a divalent group formed by an alkyl group that loses a hydrogen atom, an alkenylene group is a divalent group formed by an alkenyl group that loses a hydrogen atom, an alkynylene group is a divalent group formed by an alkynyl group that loses a hydrogen atom, an alkoxy group is a divalent group formed by an alkoxy group that loses a hydrogen atom, and an arylene group is a divalent group formed by an aryl group that loses a hydrogen atom.

In the descriptions of this application, subunit structures that are not explicitly described are interpreted in accordance with the descriptions of this paragraph.

In the descriptions of this application, a cumulative diene group refers to a group in which two double bonds share one carbon, and a structural formula of the cumulative diene group is

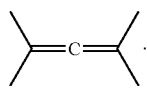

In the descriptions of this application, terms, substitutions in structural formulas, and the like that are not explicitly stated should be understood in accordance with well-known, conventional, and customary means or methods known to those of ordinary skill in the art.

The following describes the electrolyte, the electrochemical device, and the electronic device of this application in detail.

[Electrolyte]

<Additive A>

In some embodiments, the electrolyte includes an additive A, where the additive A is at least one of compounds represented by formula I-A.

formula I-A where $A^1$, $A^2$, and $A^3$ are each independently selected from formula I-B or formula I-C, and at least two of $A^1$, $A^2$, and $A^3$ are formula I-C;

formula I-B

formula I-C where in formula I-A, n is selected from integers 1 to 10, and m is selected from 0 or 1; and in formula I-B and formula I-C, represents a site at which two adjacent atoms are joined; $R^{11}$ and $R^{13}$ are each independently selected from substituted or unsubstituted $C_1$-$C_{10}$ alkylene groups, substituted or unsubstituted $C_2$-$C_{10}$ alkenylene groups, substituted or unsubstituted $C_2$-$C_{10}$ alkynylene groups, substituted or unsubstituted $C_3$-$C_{10}$ allenylene groups, substituted or unsubstituted $C_6$-$C_{10}$ arylene groups, or substituted or unsubstituted $C_3$-$C_{10}$ alicyclic hydrocarbon groups, and when substituted, a substituent group includes a halogen; and $R^{12}$ is independently selected from halogens, substituted or unsubstituted $C_1$-$C_{10}$ alkyl groups, substituted or unsubstituted $C_2$-$C_{10}$ alkenyl groups, substituted or unsubstituted $C_2$-$C_{10}$ alkynyl groups, substituted or unsubstituted $C_3$-$C_{10}$ cumulative diene groups, substituted or unsubstituted $C_6$-$C_{10}$ aryl groups, or substituted or unsubstituted $C_3$-$C_{10}$ alicyclic hydrocarbon groups, and when substituted, a substituent group includes a halogen.

In the electrolyte of this application, the additive A is a phosphine oxide polycyano functional group compound, and a cyano (—CN) functional group contained in a structure of the additive A can form a complex compound with a transition metal in a positive electrode active material of the electrochemical device, to stabilize the transition metal on a surface of the positive electrode active material. In addition, because a molecule of the additive A has a phosphine oxygen functional group, oxidation resistance of the complex compound formed by the transition metal can be improved, effectively inhibiting continuous decomposition of the electrolyte, and inhibiting gas production at a high temperature.

Therefore, the electrolyte can significantly improve high-temperature storage performance, cycle performance, and floating charge performance of the electrochemical device.
In some embodiments, the additive A includes at least one of compounds represented by formula (I-1) to formula (I-30):
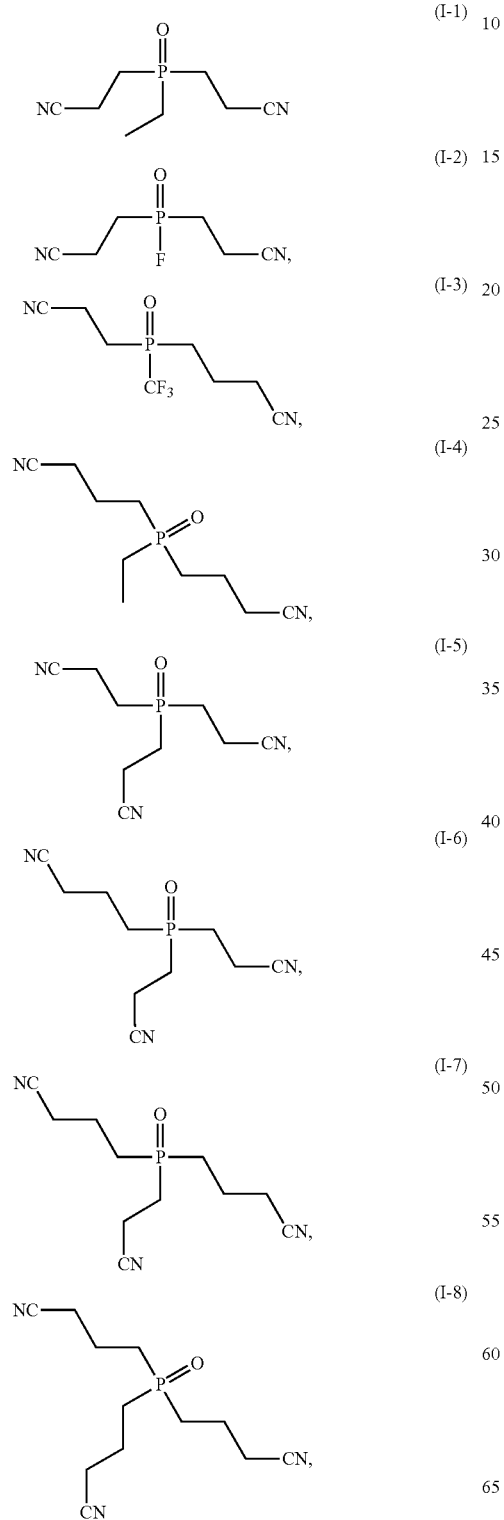
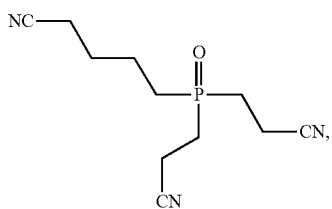
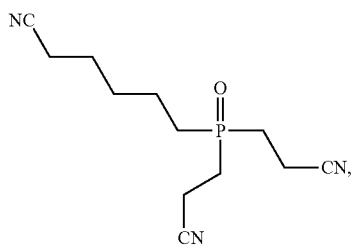
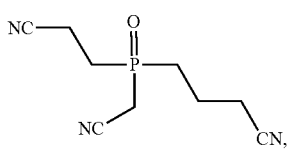
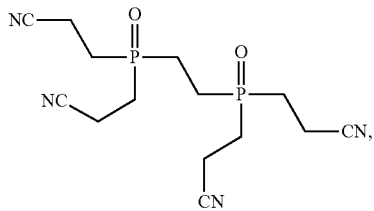
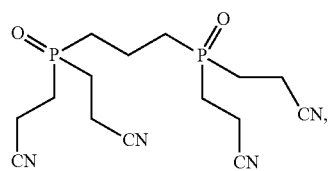
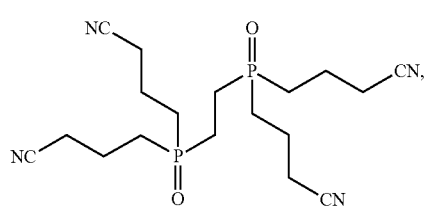
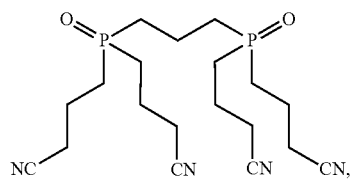

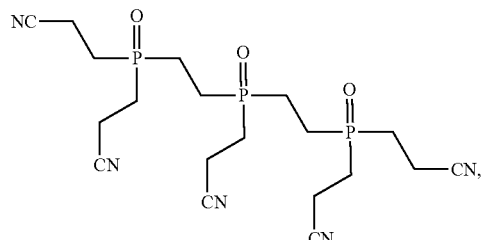
(I-16)
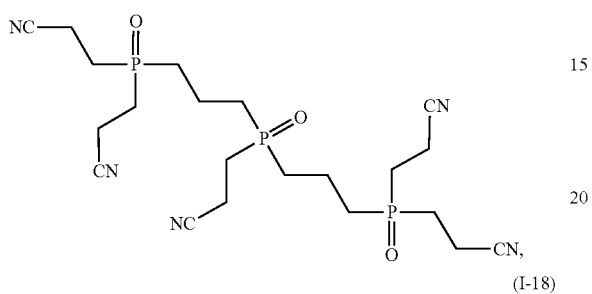
(I-17)
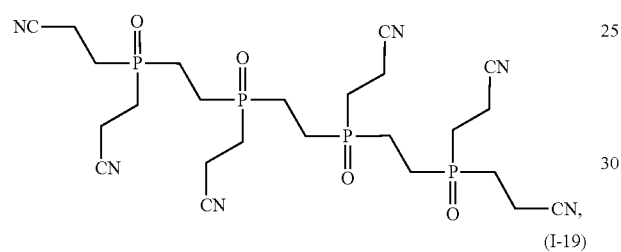
(I-18)
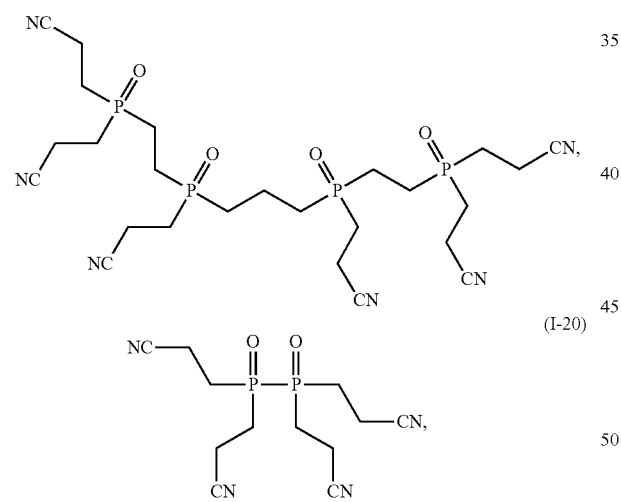
(I-19)
(I-20)
(I-21)
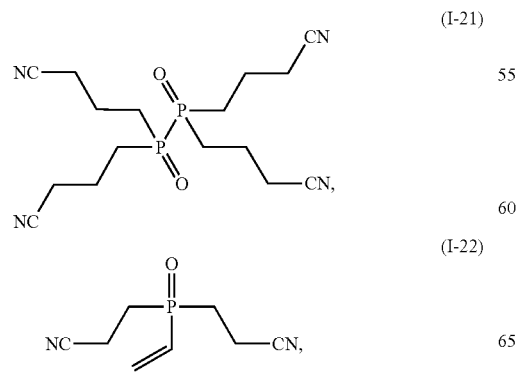
(I-22)
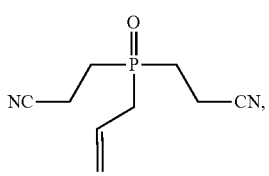
(I-23)
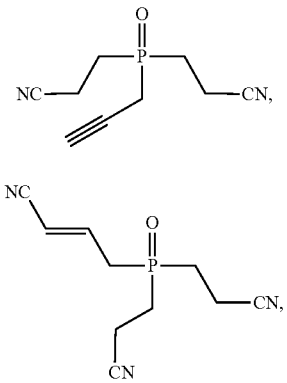
(I-24)
(I-25)
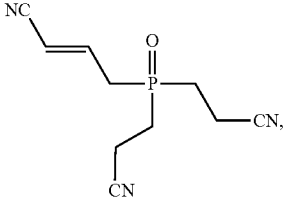
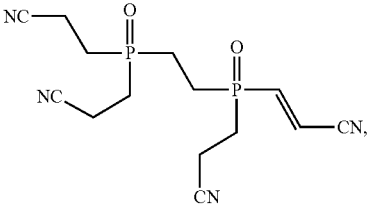
(I-26)
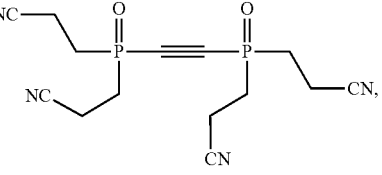
(I-27)
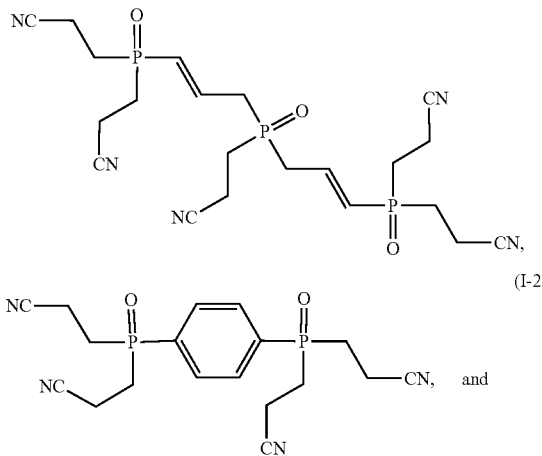
(I-28)
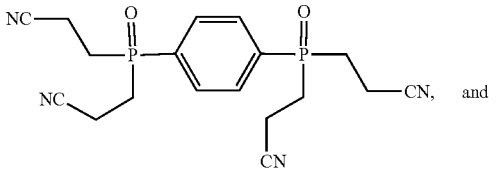
(I-29)
and

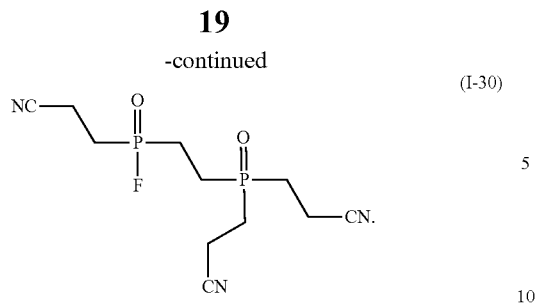
(I-30)

In some embodiments, the additive A is 0.01% to 10% of the electrolyte by mass. In some embodiments, based on the mass of the electrolyte, the mass percentage of the additive A may be 0.1%, 0.2%, 0.3%, 0.4%, 0.5%, 1.0%, 1.5%, 2.0%, 2.5%, 3.0%, 3.5%, 4.0%, 4.5%, 5.0%, 6.0%, 7.0%, 8.0%, or 9.0%.

<Additive B>

In some embodiments, the electrolyte may further include an additive B, where the additive B is at least one of compounds represented by formula II-A:

formula II-A where $R^{21}$ and $R^{22}$ are each independently selected from substituted or unsubstituted $C_1$-$C_5$ alkyl groups, substituted or unsubstituted $C_2$-$C_5$ alkenyl groups, or substituted or unsubstituted $C_2$-$C_5$ alkynyl groups, and when substituted, a substituent group includes a halogen; and $R^{21}$ and $R^{22}$ are capable of being bonded to form a cyclic structure.

The additive B is a carboxylic anhydride compound. When both the additive A and the additive B are added to the electrolyte, the high-temperature storage performance of the electrochemical device can be further improved. A possible reason is that the carboxylic anhydride may form a film on surfaces of positive and negative electrode active materials, or may neutralize alkalinity of an active material on a surface of a positive electrode, further inhibiting decomposition of the electrolyte, reducing gas production, and thereby improving the high-temperature storage performance.

In some embodiments, the additive B includes at least one of compounds represented by formula (II-1) to formula (II-22):

(II-1)

(II-2)

(II-3)

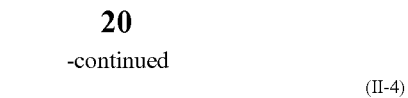
(II-4)

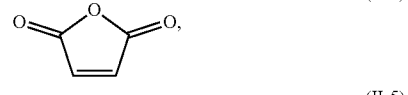
(II-5)

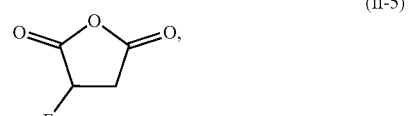
(II-6)

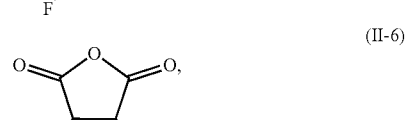
(II-7)

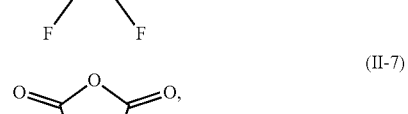
(II-8)

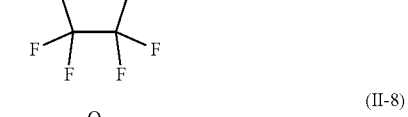
(II-9)

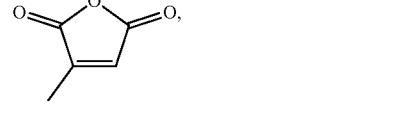
(II-10)

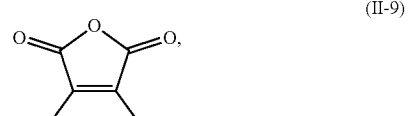
(II-11)

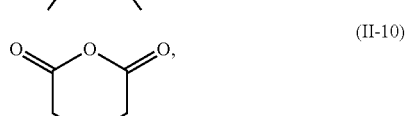
(II-12)

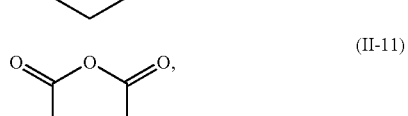
(II-13)

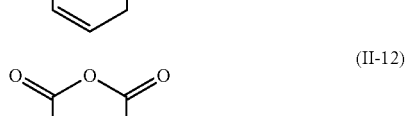
(II-14)

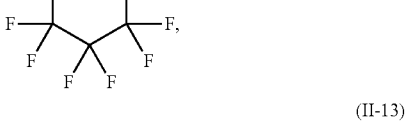
(II-15)

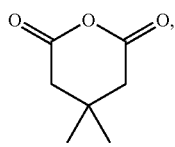 (II-16)

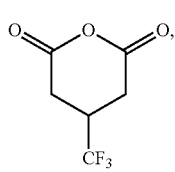 (II-17)

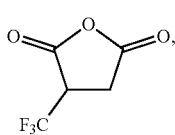 (II-18)

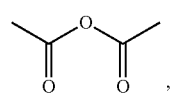 (II-19)

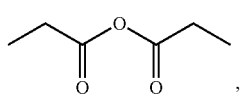 (II-20)

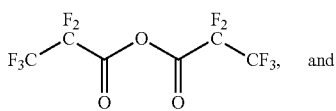 (II-21)

and

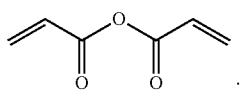 (II-22)

In some embodiments, the additive B is 0.01% to 10% of the electrolyte by mass. In some embodiments, based on the mass of the electrolyte, the mass percentage of the additive B may be 0.1%, 0.2%, 0.3%, 0.4%, 0.5%, 1.0%, 1.5%, 2.0%, 2.5%, 3.0%, 3.5%, 4.0%, 4.5%, 5.0%, 6.0%, 7.0%, 8.0%, or 9.0%.

<Additive C>

In some embodiments, the electrolyte may further include an additive C, where the additive C is at least one of compounds represented by formula III-A:

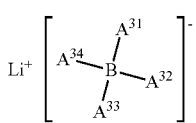 formula III-A where $A^{31}$, $A^{32}$, $A^{33}$, and $A^{34}$ are each independently selected from one of halogens, formula III-X, formula III-Y, and formula III-Z, and when formula III-Y is selected, two or four of $A^{31}$, $A^{32}$, $A^{33}$, and $A^{34}$ are selected from formula III-Y to form a cyclic structure;

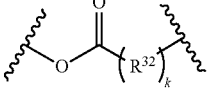 formula III-X

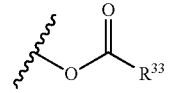 formula III-Y

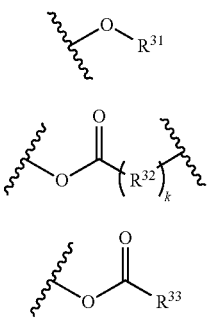 formula III-Z where $R^{31}$ and $R^{33}$ are each independently selected from substituted or unsubstituted $C_1$-$C_6$ alkyl groups, or substituted or unsubstituted $C_2$-$C_6$ alkenyl groups; $R^{32}$ is independently selected from substituted or unsubstituted $C_1$-$C_6$ alkylene groups, or substituted or unsubstituted $C_2$-$C_6$ alkenylene groups; when substituted, a substituent group includes a halogen; ⌇— represents a site at which two adjacent atoms are joined; and in formula III-Y, an O atom is connected to a B atom in formula III-A, and k is 0 or 1.

The additive C is a boron-based lithium salt compound. When both the additive A and the additive C are added to the electrolyte, the high-temperature storage performance of the electrochemical device can be further improved. A possible reason is that the boron-based lithium salt compound may form a stable interfacial film on a surface of a positive electrode active material, further reducing exposure of the positive electrode to the electrolyte, reducing the decomposition of the electrolyte, and thereby improving the high-temperature storage performance.

In some embodiments, the additive C includes at least one of lithium tetrafluoroborate ($LiBF_4$), lithium bis(oxalate)borate (LiBOB), and lithium difluoro(oxalato)borate (LiDFOB).

In some embodiments, the additive C is 0.1% to 5% of the electrolyte by mass. In some embodiments, based on the mass of the electrolyte, a mass percentage of the additive C contained in the electrolyte is 0.2%, 0.3%, 0.5%, 1%, 2%, or 3%.

<Additive D>

In some embodiments, the electrolyte may further include an additive D, where the additive D is at least one of compounds represented by formula IV-A:

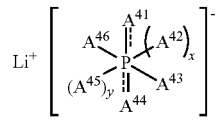 formula IV-A where ⌇ represents a single bond or a double bond, and x and y each independently represent 0 or 1; when one ⌇ in formula IV-A represents a single bond, one of x and y is 1, and the other of x and y is 0; when two ⌇ in formula IV-A both represent a single bond, both x and y are 1; when two ⌇ in formula IV-A both represent a double bond, both x and y are 0; $A^{42}$, $A^{43}$, $A^{45}$, and $A^{46}$ are each independently selected from halogens, substituted or unsubstituted $C_1$-$C_6$ alkyl groups, formula IV-B, formula IV-C, or formula IV-D, and when formula IV-C is selected, two or four of $A^{42}$, $A^{43}$, $A^{45}$, and $A^{46}$ are formula IV-C to form a cyclic structure; $A^{41}$ and $A^{44}$ are each independently selected from oxygen, halogens, substituted or unsubstituted $C_1$-$C_6$ alkyl groups, formula IV-B, formula IV-C, or formula IV-D, and when formula IV-C is selected, $A^{41}$ and $A^{44}$ both are selected from formula IV-C to form a cyclic structure; where when substituted, a substituent group includes a halogen; and $A^{41}$, $A^{42}$, $A^{43}$, $A^{44}$, $A^{45}$, and $A^{46}$ are not all fluorine.

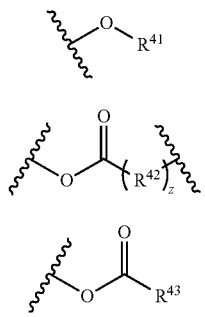

formula IV-B formula IV-C formula IV-D

In formula IV-B, formula IV-C, and formula IV-D, $R^{41}$ and $R^{43}$ are each independently selected from substituted or unsubstituted $C_1$-$C_6$ alkyl groups, or substituted or unsubstituted $C_2$-$C_6$ alkenyl groups; and $R^{42}$ is selected from substituted or unsubstituted $C_1$-$C_6$ alkylene groups, or substituted or unsubstituted $C_2$-$C_6$ alkenylene groups; where when substituted, a substituent group includes a halogen; and in formula IV-C, an O atom is connected to a P atom in formula IV-A, and z represents 0 or 1.

The additive D is a phosphorus-based lithium salt compound. When both the additive A and the additive D are added to the electrolyte, the high-temperature storage performance of the electrochemical device can be further improved. A possible reason is that the boron-based lithium salt compound may form an interfacial film on a surface of a positive electrode active material, and the interfacial film of the phosphorus-containing lithium salt compound has high oxidation resistance, which can further inhibit oxidative decomposition of the electrolyte and produce less gas, thereby improving the high-temperature storage performance.

In some embodiments, the additive D includes at least one of lithium difluorophosphate ($LiPO_2F_2$), lithium bis(oxalate) borate (LiDFOB), and lithium tetrafluoro(oxalato)phosphate (LiTFOP).

In some embodiments, the additive D is 0.1% to 5% of the electrolyte by mass. In some embodiments, based on the mass of the electrolyte, a mass percentage of the additive D contained in the electrolyte is 0.2%, 0.3%, 0.5%, 1%, 2%, or 3%.

<Additive E>

In some embodiments, the electrolyte may further include an additive E, where the additive E is at least one of compounds represented by formula V-A or formula V-B:

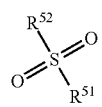

formula V-A

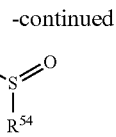

formula V-B where $R^{51}$, $R^{52}$, $R^{53}$, and $R^{54}$ are each independently selected from substituted or unsubstituted $C_1$-$C_5$ alkyl groups, substituted or unsubstituted $C_2$-$C_{10}$ alkenyl groups, substituted or unsubstituted $C_2$-$C_{10}$ alkynyl groups, substituted or unsubstituted $C_3$-$C_{10}$ alicyclic groups, substituted or unsubstituted $C_6$-$C_{10}$ aryl groups, substituted or unsubstituted $C_1$-$C_6$ alicyclic heterocyclic groups, substituted or unsubstituted $C_1$-$C_6$ aromatic heterocyclic groups, or substituted or unsubstituted $C_1$-$C_6$ heteroatom-containing functional groups, where when substituted, a substituent group includes a halogen; $R^{51}$ and $R^{52}$ are capable of being bonded to each other to form a cyclic structure; $R^{53}$ and $R^{54}$ are capable of being bonded to each other to form a cyclic structure; and a heteroatom in the heteroatom-containing functional group includes at least one of B, N, O, Si, P, and S.

The additive E is a compound containing a sulfur-oxygen double bond functional group. On the one hand, the compound containing a sulfur-oxygen double bond has a strong antioxidant capacity, making the electrolyte difficult to be oxidized on the surface of the positive electrode active material; on the other hand, the sulfur-oxygen double bond functional group containing compound can form a film on a surface of a negative electrode active material, further enhancing protection to the active material.

In some embodiments, the compound represented by formula V-A includes at least one of compounds represented by formula (V-1) to formula (V-16):

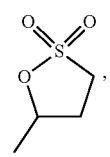

(V-1)

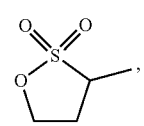

(V-2)

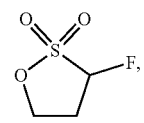

(V-3)

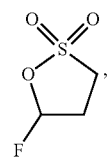

(V-4)

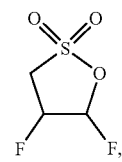

(V-5)

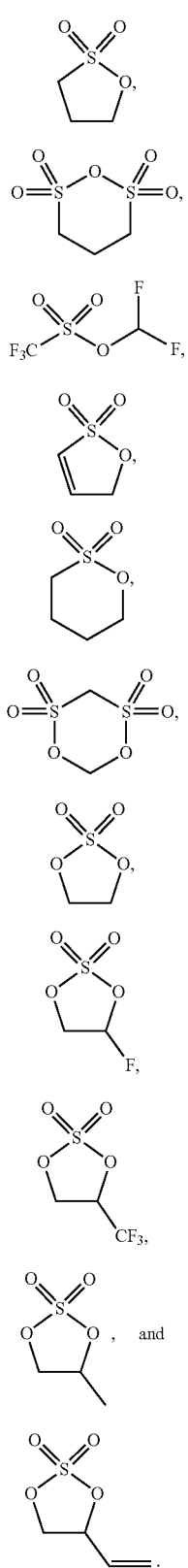

In some embodiments, the compound represented by formula V-B includes at least one of compounds represented by formula (V-17) to formula (V-20):

In some embodiments, the additive E is 0.01% to 10% of the electrolyte by mass, and preferably, 0.1% to 8%. In some embodiments, based on the mass of the electrolyte, the mass percentage of the additive E contained in the electrolyte may be 0.02%, 0.05%, 0.2%, 0.3%, 0.4%, 0.5%, 1.0%, 1.5%, 2.0%, 2.5%, 3.0%, 3.5%, 4.0%, 4.5%, 5.0%, 6.0%, 7.0%, or 9.0%.

<Additive F>

In some embodiments, the electrolyte may further include an additive F. The additive F is a multi-nitrile compound. In some embodiments, the multi-nitrile compound includes at least one of 1,2,3-tris(2-cyanoethoxy)propane, 1,3,6-hexanetricarbonitrile, 1,2-bis(2-cyanoethoxy)ethane, and adiponitrile.

When both the additive A and the additive F are added to the electrolyte, the high-temperature storage performance and cycle performance of the electrochemical device can be further improved. A possible reason is that the addition of too much additive A will cause viscosity of the electrolyte to be excessively high and affect dynamic performance of the electrochemical device, leading to deterioration of the cycle performance, while the addition of the additive F not only can effectively prevent the viscosity of the electrolyte from being too high, but also can effectively enhance stability of the positive electrode active material and further reduce the decomposition of the electrolyte, thereby improving the high-temperature storage performance and cycle performance of the electrochemical device.

In some embodiments, the additive F is 0.1% to 10% of the electrolyte by mass, and preferably, 0.5% to 5%. In some embodiments, based on the mass of the electrolyte, the mass percentage of the additive F contained in the electrolyte is 0.5%, 1.0%, 1.5%, 2.0%, 2.5%, 3.0%, 3.5%, 4.0%, 4.5%, 5.0%, 6.0%, 7.0%, or 9.0%.

In some embodiments, when both the additive A and the additive F are added to the electrolyte, a ratio of a mass percentage of the additive A to a mass percentage of the additive F is 0.01 to 1.

For the foregoing additives in this application, when the electrolyte includes the additive A, at least one of the additive B, the additive C, the additive D, the additive E, and the additive F can further be added. The combined use of the additive A and another additive in the electrolyte can further improve electrochemical performance of the electrochemical device.

<Organic Solvent>

In some embodiments, the electrolyte may further include an organic solvent. The organic solvent is an organic solvent suitable for an electrochemical device well known in the art. For example, a non-aqueous organic solvent is generally used. In some embodiments, the non-aqueous organic solvent includes at least one of a carbonate-based solvent, a carboxylate-based solvent, an ether-based solvent, a sulfone-based solvent, or another aprotic solvent.

In some embodiments, the carbonate-based solvent includes at least one of dimethyl carbonate, diethyl carbonate, ethyl methyl carbonate, methyl propyl carbonate, ethylene propyl carbonate, dipropyl carbonate, ethylene carbonate, propylene carbonate, and butylene carbonate.

In some embodiments, the carboxylate-based solvent includes at least one of methyl formate, ethyl formate, ethyl acetate, propyl acetate, butyl acetate, methyl propionate, ethyl propionate, propyl propionate, 2,2-difluoroethyl acetate, 2,2-di Ethyl fluoroacetate, γ-butyrolactone, valerolactone, and butyrolactone.

In some embodiments, the ether-based solvent includes at least one of ethylene glycol dimethyl ether, diethylene glycol dimethyl ether, tetraethylene glycol dimethyl ether, dibutyl ether, tetrahydrofuran, and 2-methyltetrahydrofuran.

In some embodiments, the sulfone-based solvent includes at least one of ethyl vinyl sulfone, methyl isopropyl sulfone, isopropyl sec-butyl sulfone, and sulfolane.

In this application, the organic solvent in the electrolyte may be a non-aqueous organic solvent, or may be a mixture of a plurality of non-aqueous organic solvents. When a mixed solvent is used, electrochemical device with different properties can be obtained by controlling a mixing ratio.

<Electrolyte Salt>

In some embodiments, the electrolyte further includes an electrolyte salt. The electrolyte salt is an electrolyte salt suitable for an electrochemical device well known in the art. Suitable electrolyte salts can be selected depending on electrochemical devices. For a lithium-ion battery, for example, a lithium salt is generally used as an electrolyte salt.

In some embodiments, the lithium salt includes at least one of an organic lithium salt or an inorganic lithium salt.

In some embodiments, the lithium salt used for this application contains at least one of fluorine and phosphorus.

In some embodiments, the lithium salt of this application includes at least one of lithium hexafluorophosphate ($LiPF_6$) and lithium di(fluorosulfonyl)imide ($LiN(C_yF_{2y+1}SO_2)$ $(C_zF_{2z+1}SO_2)$, where y and z are natural numbers).

In some embodiments, based on a total volume of the electrolyte, a concentration of the lithium salt in the electrolyte is approximately 0.5 mol/L to 3 mol/L, preferably, approximately 0.5 mol/L to 2 mol/L, and more preferably, approximately 0.8 mol/L to 1.5 mol/L.

In this application, a preparation method of the electrolyte is not limited, and the electrolyte can be prepared according to the conventional preparation method of the electrolyte well known to those skilled in the art.

[Electrochemical Device]

The following describes the electrochemical device of this application.

The electrochemical device of this application is, for example, a primary battery, a secondary battery, a fuel cell, a solar cell, or a capacitor. The secondary battery is, for example, a secondary lithium battery, and the secondary lithium battery includes, but is not limited to, a secondary lithium metal battery, a secondary lithium-ion battery, a secondary lithium polymer battery, or a secondary lithium-ion polymer battery.

In some embodiments, the electrochemical device includes a positive electrode plate, a negative electrode plate, a separator, and the foregoing electrolyte in this application.

In some embodiments, a charge cut-off voltage of the electrochemical device of this application is not less than 4.2 V.

<Positive Electrode Plate>

The positive electrode plate is a positive electrode plate well known in the art that can be used in an electrochemical device. In some embodiments, the positive electrode plate includes a positive electrode current collector and a positive electrode active material layer disposed on the positive electrode current collector. The positive electrode active material layer includes a positive electrode active material, a positive electrode conductive agent, and a positive electrode binder.

Various substances conventionally well known in the art that can be used as positive electrode active materials of the electrochemical device and that is capable of reversibly intercalating or deintercalating active ions can be selected as the positive electrode active material. In some embodiments, the positive electrode active material includes a composite oxide containing lithium and at least one selected from cobalt, manganese, and nickel.

In some embodiments, the positive electrode active material includes:

at least one of $Li_aA_{1-b}B_bD_2$ (where $0.90 \leq a \leq 1.8$, $0 \leq b \leq 0.5$), $Li_aE_{1-b}B_bO_{2-c}D_c$ (where $0.90 \leq a \leq 1.8$, $0 \leq b \leq 0.5$, and $0 \leq c \leq 0.05$), $LiE_{2-b}B_bO_{4-c}D_c$ (where $0 \leq b \leq 0.5$, and $0 \leq c \leq 0.05$), $Li_aNi_{1-b-c}Co_bB_cD_\alpha$ (where $0.90 \leq a \leq 1.8$, $0 \leq b \leq 0.5$, $0 \leq c \leq 0.05$, and $0 < \alpha \leq 2$), $Li_aNi_{1-b-c}Co_bB_cO_{2-\alpha}F_\alpha$ (where $0.90 \leq a \leq 1.8$, $0 \leq b \leq 0.5$, $0 \leq c \leq 0.05$, and $0 < \alpha < 2$), $Li_aNi_{1-b-c}Co_bB_cO_{2-\alpha}F_2$ (where $0.90 \leq a \leq 1.8$, $0 \leq b \leq 0.5$, $0 \leq c \leq 0.05$, and $0 < \alpha < 2$), $Li_aNi_{1-b-c}Mn_bB_cD_\alpha$ (where $0.90 \leq a \leq 1.8$, $0 \leq b \leq 0.5$, $0 \leq c \leq 0.05$, and $0 < \alpha < 2$), $Li_aNi_{1-b-c}Mn_bB_cO_{2-\alpha}F_\alpha$ (where $0.90 \leq a \leq 1.8$, $0 \leq b \leq 0.5$, $0 \leq c \leq 0.05$, and $0 < \alpha < 2$), $Li_aNi_{1-b-c}Mn_bB_cO_{2-\alpha}F_2$ (where $0.90 \leq a \leq 1.8$, $0 \leq b \leq 0.5$, $0 \leq c \leq 0.05$, and $0 < \alpha < 2$), $Li_aN_{ib}E_cG_dO_2$ (where $0.90 \leq a \leq 1.8$, $0 \leq b \leq 0.9$, $0 \leq c \leq 0.5$, and $0.001 \leq d \leq 0.1$), $Li_aNi_bCo_cMn_dG_eO_2$ (where $0.90 \leq a \leq 1.8$, $0 \leq b \leq 0.9$, $0 \leq c \leq 0.5$, $0 \leq d \leq 0.5$, and $0.001 \leq e \leq 0.1$), $Li_aNiG_bO_2$ (where $0.90 \leq a \leq 1.8$, and $0.001 \leq b \leq 0.1$), $Li_aCoG_bO_2$ (where $0.90 \leq a \leq 1.8$, and $0.001 \leq b \leq 0.1$), $Li_aMnG_bO_2$ (where $0.90 \leq a \leq 1.8$, and $0.001 \leq b \leq 0.1$), $Li_aMn_2G_bO_4$ (where $0.90 \leq a \leq 1.8$, and $0.0010.1$), $QO_2$, $QS_2$, $LiQS_2$, $V_2O_5$, $LiV_2O_5$, $LiIO_2$, $LiNiVO_4$, $Li_{3-f}J_2(PO_4)_3$ (where $0 \leq f \leq 2$), $Li_{3-f}Fe_2(PO_4)_3$ (where $0 \leq f \leq 2$), and $LiFePO_4$.

In the foregoing chemical formulas, A is Ni, Co, Mn, or a combination thereof; B is Al, Ni, Co, Mn, Cr, Fe, Mg, Sr, V, a rare earth element, or a combination thereof; D is O, F, S, P, or a combination thereof; E is Co, Mn, or a combination thereof; F is F, S, P, or a combination thereof; G is Al, Cr, Mn, Fe, Mg, La, Ce, Sr, V, or a combination thereof; Q is Ti, Mo, Mn, or a combination thereof; I is Cr, V, Fe, Sc, Y, or a combination thereof; and J is V, Cr, Mn, Co, Ni, Cu, or a combination thereof.

In some embodiments, $D_v10$ of the positive electrode active material is not more than 18 μm.

In some embodiments, a specific surface area BET of the positive electrode active material is not greater than 0.5 m²/g.

The positive electrode conductive agent is used to provide conductivity for a positive electrode and can improve the conductivity of the positive electrode. The positive electrode conductive agent is a conductive material well known in the art that can be used as a positive electrode active material layer. The positive electrode conductive agent may be selected from any conductive material that causes no chemical change. In some embodiments, the positive electrode conductive agent includes at least one of a carbon-based material (for example, natural graphite, artificial graphite, carbon black, acetylene black, Ketjen black, and carbon fiber), a metal-based material (for example, metal powder or metal fiber including copper, nickel, aluminum, silver, and the like), and a conductive polymer (for example, a polyphenylene derivative).

The positive electrode binder is a binder well known in the art that can be used as a positive electrode active material layer. The positive electrode binder can improve binding performance between positive electrode active material particles and between the positive electrode active material particles and the positive electrode current collector. In some embodiments, the positive electrode binder includes at least one of polyvinyl alcohol, carboxymethyl cellulose, hydroxypropyl cellulose, diacetyl cellulose, polyvinyl chloride, carboxylated polyvinyl chloride, polyvinyl fluoride, a polymer containing ethylene oxide, polyvinylpyrrolidone, polyurethane, polytetrafluoroethylene, polyvinylidene fluoride, polyethylene, polypropylene, styrene-butadiene rubber, acrylic styrene-butadiene rubber, epoxy resin, and nylon.

In some embodiments, a compacted density of the positive electrode active material layer is less than 4.5 g/cm³. In some embodiments, the compacted density of the positive electrode active material layer is 4.0 g/cm³ to 4.3 g/cm³.

The positive electrode current collector is a metal. In some embodiments, the metal is, for example, but is not limited to, an aluminum foil.

In some embodiments, a structure of the positive electrode plate is a structure of a positive electrode plate well known in the art that can be used in the electrochemical device.

In some embodiments, a preparation method of the positive electrode plate is a preparation method of a positive electrode plate well known in the art that can be used in the electrochemical device. In some embodiments, in preparation of a positive electrode slurry, a positive electrode active material and a binder were usually added, and a conductive material and a thickener were added as needed and then dissolved or dispersed in a solvent to make the positive electrode slurry. The solvent was volatilized and removed during drying. The solvent is a solvent well known in the art that can be used as a positive electrode active material layer. For example, the solvent is, but not limited to, N-methylpyrrolidone (NMP).

<Negative Electrode Plate>

The negative electrode plate is a negative electrode plate well known in the art that can be used in an electrochemical device. In some embodiments, the negative electrode plate includes a negative electrode current collector and a negative electrode active material layer disposed on the negative electrode current collector. The negative electrode active material layer includes a negative electrode active material, a negative electrode conductive agent, and a negative electrode binder.

The negative electrode active material can be selected from various materials conventionally well known in the art that can be used as negative electrode active materials of the electrochemical device and that is capable of intercalating or deintercalating active ions, or materials well known in the art that is capable of doping and dedoping active ions.

In some embodiments, the negative electrode active material includes at least one of lithium metal, a lithium metal alloy, a material capable of doping/dedoping lithium, a transition metal oxide, and a carbon material.

In some embodiments, the lithium metal alloy includes lithium and at least one selected from Na, K, Rb, Cs, Fr, Be, Mg, Ca, Sr, Si, Sb, Pb, In, Zn, Ba, Ra, Ge, Al, or Sn.

In some embodiments, the material capable of doping/dedoping lithium includes at least one of Si, $SiO_x$ (where 0<x<2), a Si/C composite, a Si-Q alloy (where Q is not Si and is an alkali metal, an alkaline earth metal, an element from group 13 to group 16, a transition element, a rare earth element, or a combination thereof), Sn, $SnO_z$ (where 0<z<2), a Sn/C composite, or a Sn—R alloy (where R is not Sn and is an alkali metal, an alkaline earth metal, an element from group 13 to group 16, a transition element, a rare earth element, or a combination thereof).

Example elements of Q and R may be at least one of Mg, Ca, Sr, Ba, Ra, Sc, Y, Ti, Zr, Hf, Rf, V, Nb, Ta, db, Cr, Mo, W, Sg, Tc, Re, Bh, Fe, Pb, Ru, Os, Hs, Rh, Ir, Pd, Pt, Cu, Ag, Au, Zn, Cd, B, Al, Ga, Sn, In, Tl, Ge, P, As, Sb, Bi, S, Se, Te, and Po.

In some embodiments, $SiO_x$ (where 0<x<2) is a porous silicon negative electrode active material, and an average particle size D50 of the porous $SiO_x$ particles ranges from 1 μm to 20 μm. In some embodiments, when measurement is performed on the surface, an average diameter of pores in the SiOx particles is 30 nm to 500 nm, and a specific surface area of the $SiO_x$ particles is 5 m²/g to 50 m²/g. In some embodiments, the $SiO_x$ particle silicon negative electrode active material may further include at least one of $Li_2SiO_3$ and $Li_4SiO_4$.

In some embodiments, the carbon in the Si/C composite is not aggregated in bulk or dispersed in the Si particles, but is uniformly dispersed in the Si particles in an atomic state. In some embodiments, a molar ratio of C to Si (that is, C/Si) may fall within the range of greater than 0 and less than 18. In some embodiments, a percentage of carbon contained in the Si/C composite may be 1% to 50% with respect to an overall weight of the Si/C composite. In some embodiments, a particle size of the Si/C composite may be 10 nm to 100 μm.

Various carbon materials known in the art that can be used as a carbon-based negative electrode active material of the electrochemical device can be selected as a carbon material. In some embodiments, the carbon material includes at least one of crystalline carbon and amorphous carbon. In some embodiments, the crystalline carbon is natural graphite or artificial graphite. In some embodiments, the crystalline carbon is amorphous, plate-shaped, platelet-shaped, spherical, or fiber-shaped. In some embodiments, the crystalline carbon is low crystalline carbon and high crystalline carbon. In some embodiments, the low crystalline carbon includes at least one of soft carbon and hard carbon. In some embodiments, the high crystalline carbon includes at least one of natural graphite, crystalline graphite, pyrolytic carbon, mesophase pitch-based carbon fiber, mesophase carbon microbeads, mesophase pitch, and high-temperature calcined carbon. In some embodiments, the high-temperature calcined carbon is petroleum or coke derived from coal tar pitch. In some embodiments, the amorphous carbon includes at least one of soft carbon, hard carbon, a mesophase pitch carbonization product, and fired coke.

The negative electrode conductive agent is used to provide conductivity for a negative electrode and can improve the conductivity of the negative electrode. The negative electrode conductive agent is a conductive material well known in the art that can be used as a negative electrode active material layer. The negative electrode conductive agent may be selected from any conductive material that causes no chemical change. In some embodiments, the negative electrode conductive agent includes at least one of a carbon-based material (for example, natural graphite, artificial graphite, conductive carbon black, acetylene black, Ketjen black, and carbon fiber), a metal-based material (for example, metal powder or metal fiber including copper, nickel, aluminum, silver, and the like), and a conductive polymer (for example, a polyphenylene derivative).

The negative electrode binder is a binder well known in the art that can be used as a negative electrode active material layer. In some embodiments, the negative electrode binder includes at least one of poly(vinylidene fluoride-co-hexafluoropropene) (PVDF-co-HFP), polyvinylidene fluoride, polyacrylonitrile, polymethyl methacrylate, polyvinyl alcohol, carboxymethyl cellulose, hydroxypropyl cellulose, polyvinyl chloride, carboxylated polyvinyl chloride, polyvinyl fluoride, a polymer containing ethylene oxide, polyvinylpyrrolidone, polyurethane, polytetrafluoroethylene, polyethylene, polypropylene, styrene butadiene rubber, acrylic(ester)styrene butadiene rubber, epoxy resin, and nylon.

The negative electrode current collector is a metal. In some embodiments, for example, the negative electrode current collector includes, but is not limited to, copper foil, nickel foil, stainless steel foil, titanium foil, nickel foam, copper foam, a polymer substrate coated with a conductive metal, and any combination thereof.

In some embodiments, a structure of the negative electrode plate is a structure of a negative electrode plate well known in the art that can be used in the electrochemical device.

In some embodiments, a preparation method of the negative electrode plate is a preparation method of a negative electrode plate well known in the art that can be used in the electrochemical device. In some embodiments, in preparation of a negative electrode slurry, a negative electrode active material and a binder were usually added, and a conductive material and a thickener were added as needed and then dissolved or dispersed in a solvent to make the negative electrode slurry. The solvent was volatilized and removed during drying. The solvent is a solvent well known in the art that can be used as a negative electrode active material layer, for example, but not limited to water. The thickener is a thickener well known in the art that can be used as a negative electrode active material layer, for example, but not limited to sodium carboxymethyl cellulose.

<Separator>

The separator is a separator well known in the art that can be used in the electrochemical device, for example, but not limited to a polyolefin-based porous film. In some embodiments, the polyolefin-based porous film may be selected from a single-layer or multi-layer film composed of one or more of polyethylene (PE), ethylene-propylene copolymer, polypropylene (PP), ethylene-butene copolymer, ethylene-hexene copolymer, and ethylene-methyl methacrylate copolymer.

In some embodiments, the polyolefin-based porous film is coated with a coating layer. In some embodiments, the coating layer includes an organic coating layer and an inorganic coating layer. In some embodiments, the organic coating layer includes at least one of polyvinylidene fluoride, vinylidene fluoride-hexafluoropropylene copolymer, polyacrylonitrile, polyimide, acrylonitrile-butadiene copolymer, acrylonitrile-styrene-butadiene copolymer, polymethyl methacrylate, polymethyl acrylate, polyethyl acrylate, acrylic acid-styrene copolymer, polydimethylsiloxane, sodium polyacrylate, and sodium carboxymethyl cellulose. In some embodiments, the inorganic coating layer includes at least one of $SiO_2$, $Al_2O_3$, $CaO$, $TiO_2$, $ZnO_2$, $MgO$, $ZrO_2$, and $SnO_2$.

This application does not specifically limit the shape and thickness of the separator. A preparation method of the separator is a preparation method of a separator well known in the art that can be used in the electrochemical device.

<Outer Package Shell>

In some embodiments, the electrochemical device further includes an outer package shell. The outer package shell is an outer package shell well known in the art that can be used for the electrochemical device and is stable to the used electrolyte, for example, but not limited to a metal-type outer package shell.

[Electronic Device]

The following describes the electronic device of this application.

The electronic device of this application is any electronic device, for example, but not limited to: a notebook computer, a pen-input computer, a portable computer, an e-book player, a mobile phone, a portable fax machine, a portable copier, a portable printer, a head-mounted stereo headset, a video recorder, a liquid crystal display television, a portable cleaner, a portable CD player, a mini disc, a transceiver, an electronic notebook, a calculator, a memory card, a portable recorder, a radio, a backup power supply, a motor, an automobile, a motorcycle, an assisted bicycle, a bicycle, a lighting apparatus, a toy, a game console, a clock, an electric tool, a flashlight, a camera, a large household storage battery, or a lithium-ion capacitor. It should be noted that the electrochemical device of this application is not only applicable to the electronic devices listed above, but also applicable to energy storage power stations, marine transport vehicles, and air transport vehicles. The air transport vehicles include air transport vehicles inside the atmosphere and air transport vehicles outside the atmosphere.

In some embodiments, the electronic device includes the foregoing electrochemical device in this application.

The following further describes this application with reference to embodiments. In the following specific examples of this application, only an example in which the battery is a lithium-ion battery is shown, but this application is not limited thereto. In the following examples and comparative examples, all reagents, materials, and instruments used are commercially or synthetically available unless otherwise specified.

The specific compounds used in the examples are as follows.

Additive A:

(I-5) [structure: tris(2-cyanoethyl)phosphine oxide]

(I-11) [structure]

(I-12) [structure]

(I-16) [structure]

(I-18) [structure]

(I-21) [structure]

(I-23) [structure]

(I-27) [structure], and (I-30) [structure].

Additive B:

(II-8) [structure]

citrate anhydride (II-9) [structure]

2,3-dimethylmaleic anhydride

Additive C:
lithium tetrafluoroborate (LiBF$_4$), and lithium difluoro(oxalato)borate (LiDFOB).

Additive D:
lithium difluorophosphate (LiPO$_2$F$_2$), and lithium tetrafluoro(oxalato)phosphate (LiTFOP).

Additive E:

(V-2) [structure]

2,4-butanesultone (V-6) [structure]

1,3-propane sultone

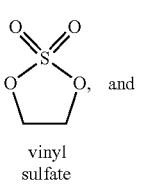

vinyl sulfate (V-12)

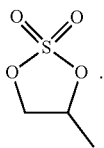

4-methyl vinyl sulfate (V-15)

Additive F:

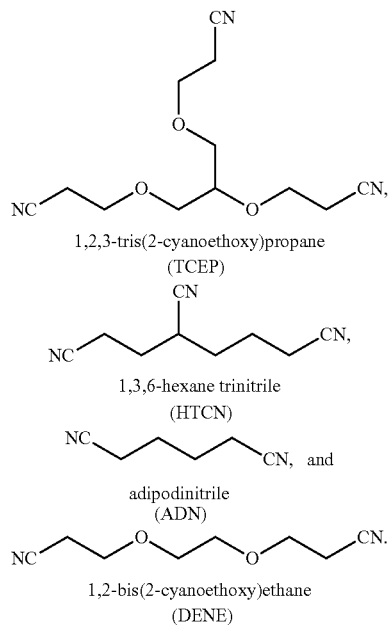

1,2,3-tris(2-cyanoethoxy)propane (TCEP)

1,3,6-hexane trinitrile (HTCN)

adipodinitrile (ADN)

1,2-bis(2-cyanoethoxy)ethane (DENE)

The lithium-ion batteries in Examples 1 to 62 and Comparative Examples 1 to 6, Examples S1 to S11 and Comparative Examples S' were all prepared according to the following method.

(1) Preparation of an Electrolyte

In an argon atmosphere glove box with a water content of less than 10 ppm, ethylene carbonate (EC for short), propylene carbonate (PC for short), diethyl carbonate (DEC for short), ethyl propionate (EP for short), and propyl propionate (PP for short) were mixed uniformly at a mass ratio of 1:1:1:1:1 into a non-aqueous organic solvent, and a fully dried lithium salt $LiPF_6$ (1 M) was then dissolved in the non-aqueous organic solvent, to form a basic electrolyte. A specified amount of additive was added to the basic electrolyte to prepare the electrolyte in Examples 1 to 62, Comparative Examples 1 to 6, Examples S1 to S11, and Comparative Example S'.

(2) Preparation of a Positive Electrode Plate

A positive electrode active material LCO (whose molecular formula was $LiCoO_2$), conductive carbon black, and a binder polyvinylidene fluoride (PVDF for short) were fully stirred and mixed at a weight ratio of 97.9:0.9:1.2 in an appropriate amount of N-methylpyrrolidone (NMP for short) solvent to form a uniform positive electrode slurry. The slurry was applied on a positive electrode current collector Al foil, and then dried and cold pressed to obtain a positive electrode plate.

(3) Preparation of a Negative Electrode Plate

A negative electrode active material graphite, a binder styrene butadiene rubber (SBR for short), and a thickener sodium carboxymethyl cellulose (CMC for short) were fully stirred and mixed at a weight ratio of 97.4:1.4:1.2 in an appropriate amount of deionized water solvent to form a uniform negative electrode slurry. The slurry was applied on a negative electrode current collector Cu foil, and then dried and cold pressed to obtain a negative electrode plate.

(4) Preparation of a Separator

A PE porous polymer film was used as a separator.

(5) Preparation of a Lithium-Ion Battery

The prepared positive electrode plate, the separator, and the negative electrode plate were laminated in sequence, so that the separator was sandwiched between the positive electrode plate and the negative electrode plate to provide separation. Then the laminated product was wound to obtain an electrode assembly. The electrode assembly was placed in an outer package foil, leaving a liquid injection port. The prepared electrolyte was poured from the liquid injection port. Then, after vacuum packaging, standing, chemical conversion, shaping, and other processes, a lithium-ion battery was obtained.

Next, the following describes a performance test process of the lithium-ion batteries in Examples 1 to 62, Comparative Examples 1 to 6, Examples S1 to S11, and Comparative Example S'.

(1) High-Temperature Storage Performance Test at 4.45 V

The battery was charged to 4.45 V at a constant current of 0.5 C at 25° C., and then charged to a current of 0.05 C at a constant voltage. A thickness of the lithium-ion battery was measured and recorded as d0. Then the lithium-ion battery was placed in an oven at 85° C. for 24 h, and the thickness of the lithium-ion battery at this time was measured and recorded as d. A thickness swelling rate (%) of the lithium-ion battery after high-temperature storage for 24 h was (d−d0)/d0×100%. If the thickness swelling rate exceeded 50%, the test was stopped.

(2) High-Temperature Storage Performance Test at 4.5 V

The battery was charged to 4.5 V at a constant current of 0.5 C at 25° C., and then charged to a current of 0.05 C at a constant voltage. A thickness of the lithium-ion battery was measured and recorded as d0. Then the lithium-ion battery was placed in an oven at 85° C. for 24 h, and the thickness of the lithium-ion battery at this time was measured and recorded as d. A thickness swelling rate (%) of the lithium-ion battery after high-temperature storage for 24 h was (d−d0)/d0×100%. If the thickness swelling rate exceeded 50%, the test was stopped.

(3) Cycle Performance Test

The battery was charged to 4.45 V at 0.7 C at 25° C., and then charged to 0.05 C at a constant voltage at 4.45 V. After that, the battery was discharged to 3.0 V at a current of 1 C, a process of charging at 0.7 C and discharging at 1 C was repeated for 800 cycles, and a current capacity retention rate was recorded.

(4) Floating Charge Performance Test

The battery was discharged to 3.0 V at 0.5 C at 25° C., charged to 4.45 V at 0.5 C, and then charged to 0.05 C at a constant voltage of 4.45 V. A thickness of the lithium-ion battery was measured and recorded as d0. The battery was placed in an oven at 45° C., and charged at a constant voltage of 4.45 V for 42 days. The thickness of the battery was monitored and recorded as d. A thickness swelling rate (%) for floating charge of the lithium-ion battery was (d−d0)/d0×100%.

Types and contents of the additives in the electrolyte and the performance test results of the lithium-ion batteries that are used in Examples 1 to 62, Comparative Examples 1 to 6, Examples S1 to S11, and Comparative Example S' are shown in Tables 1 to 4 separately. The content of each additive is a mass percentage calculated based on a mass of the electrolyte.

increased, a degree of improvement first increased and then decreased, and finally tended to be stable. The compounds I-11, I-12, and I-30, used as the additive A, also improved the high-temperature storage performance and cycle performance of the lithium batteries at different charge cut-off voltages to different degrees. When the additive E was added to the electrolyte containing the additive A, the high-temperature storage performance and cycle performance of the lithium batteries at different charge cut-off voltages were further improved.

Although the additive in Comparative Example 1 also contained a cyano group and a phosphinooxy group, the

TABLE 1

| Example | Additive A Compound | Additive A Content (wt %) | Additive E Compound | Additive E Content (wt %) | Compound | Content (wt %) | Thickness swelling rate after storage for 24 h at 4.45 V and 85° C. | Thickness swelling rate after storage for 24 h at 4.5 V and 85° C. | Capacity retention rate after 800 cycles at 25° C. |
|---|---|---|---|---|---|---|---|---|---|
| Example 1 | I-5 | 0.1 | | | | | 32.50% | 48.60% | 74.50% |
| Example 2 | I-5 | 0.3 | | | | | 29.30% | 44.50% | 80.30% |
| Example 3 | I-5 | 0.5 | | | | | 24.90% | 38.90% | 83.60% |
| Example 4 | I-5 | 1 | | | | | 18.60% | 32.30% | 84.20% |
| Example 5 | I-5 | 3 | | | | | 15.30% | 25.70% | 83.60% |
| Example 6 | I-5 | 5 | | | | | 9.60% | 16.20% | 76.60% |
| Example 7 | I-11 | 0.5 | | | | | 22.10% | 36.80% | 83.30% |
| Example 8 | I-12 | 0.5 | | | | | 19.80% | 34.30% | 85.50% |
| Example 9 | I-16 | 0.5 | | | | | 17.20% | 30.20% | 86.20% |
| Example 10 | I-18 | 0.5 | | | | | 16.90% | 28.70% | 85.80% |
| Example 11 | I-21 | 0.5 | | | | | 18.90% | 32.50% | 84.30% |
| Example 12 | I-23 | 0.5 | | | | | 22.30% | 35.30% | 86.70% |
| Example 13 | I-27 | 0.5 | | | | | 20.50% | 32.90% | 85.20% |
| Example 14 | I-30 | 0.5 | | | | | 20.90% | 35.20% | 81.40% |
| Example 15 | I-5 | 0.5 | V-2 | 2 | | | 23.20% | 37.00% | 84.50% |
| Example 16 | I-5 | 0.5 | V-2 | 3 | V-12 | 0.5 | 21.40% | 35.30% | 85.20% |
| Example 17 | I-5 | 0.5 | V-2 | 4 | V-12 | 0.5 | 20.20% | 34.00% | 86.10% |
| Example 18 | I-5 | 0.5 | V-2 | 4 | V-12 | 1 | 18.80% | 32.60% | 85.50% |
| Example 19 | I-5 | 0.5 | V-6 | 3 | V-15 | 1 | 20.50% | 34.70% | 85.50% |
| Example 20 | I-5 | 0.5 | V-6 | 4 | V-15 | 0.5 | 19.90% | 33.60% | 86.70% |
| Example 21 | I-5 | 0.5 | V-6 | 4 | V-12 | 0.5 | 19.50% | 33.70% | 86.50% |
| Example 22 | I-11 | 0.5 | V-2 | 4 | V-12 | 0.5 | 18.30% | 32.30% | 85.50% |
| Example 23 | I-12 | 0.5 | V-2 | 4 | V-12 | 0.5 | 15.50% | 30.70% | 88.30% |
| Example 24 | I-16 | 0.5 | V-2 | 4 | V-12 | 0.5 | 14.20% | 25.60% | 87.60% |
| Example 25 | I-18 | 0.5 | V-2 | 4 | V-12 | 0.5 | 13.70% | 24.40% | 86.70% |
| Example 26 | I-21 | 0.5 | V-2 | 4 | V-12 | 0.5 | 16.30% | 28.50% | 85.90% |
| Example 27 | I-30 | 0.5 | V-2 | 4 | V-12 | 0.5 | 16.80% | 31.20% | 84.20% |
| Example 28 | I-11 | 0.5 | V-6 | 4 | V-15 | 0.5 | 18.10% | 31.50% | 86.20% |
| Example 29 | I-12 | 0.5 | V-6 | 4 | V-15 | 0.5 | 16.00% | 29.80% | 88.20% |
| Example 30 | I-23 | 0.5 | V-6 | 4 | V-15 | 0.5 | 18.10% | 30.20% | 87.90% |
| Example 31 | I-30 | 0.5 | V-6 | 4 | V-15 | 0.5 | 16.90% | 30.00% | 84.10% |
| Example 32 | I-11 | 0.5 | V-6 | 4 | V-12 | 0.5 | 16.20% | 31.80% | 86.50% |
| Example 33 | I-12 | 0.5 | V-6 | 4 | V-12 | 0.5 | 15.80% | 29.00% | 88.00% |
| Example 34 | I-27 | 0.5 | V-6 | 4 | V-12 | 0.5 | 16.70% | 28.00% | 87.90% |
| Example 35 | I-30 | 0.5 | V-6 | 4 | V-12 | 0.5 | 16.10% | 30.50% | 83.90% |
| Comparative Example 1 | Propionitrile + Triethylphosphine Oxide | 1.5+ 0.5 | | | | | 40.20% | >50% | 59.60% |
| Comparative Example 2 | | | V-6 | 4 | V-12 | 0.5 | 37.60% | >50% | 69.30% |

Note:
The blank space in Table 1 means that no addition of the corresponding additive.

It can be seen from Examples and Comparative Examples in Table 1 that, the compound I-5, used as the additive A, not only could improve the high-temperature storage performance of the lithium-ion batteries at 4.45 V, but also could improve the high-temperature storage performance of the lithium-ion batteries at 4.5 V and significantly improve cycle performance of the batteries. Different charge cut-off voltages led to different improvement effects. As the content high-temperature storage performance and cycle performance of the battery were far inferior to those in the example containing the additive A. A possible reason is that the additive A is a phosphinooxy polycyano functional group compound. A cyano group (—CN) functional group contained in a structure of the additive A can form a complex compound with a transition metal in the positive electrode active material, which can stabilize the transition metal on the surface of the positive electrode active material. In addition, due to the phosphinooxy functional group in the molecule, the phosphinooxy functional group can be attached to the surface of the positive electrode active material along with the cyano group to improve oxidation resistance of the complex compound formed by the transition metal, thereby effectively inhibiting continuous decomposition of the electrolyte and high-temperature gas generation.

TABLE 2

| | Additive A | | Additive C | | Thickness swelling rate after storage for 24 h at 4.5 V and 85° C. |
|---|---|---|---|---|---|
| Example | Compound | Content (wt %) | Compound | Content (wt %) | |
| Example 3 | I-5 | 0.5 | | | 38.90% |
| Example 36 | I-5 | 0.5 | LiBF$_4$ | 0.1 | 36.80% |
| Example 37 | I-5 | 0.5 | LiBF$_4$ | 0.2 | 34.20% |
| Example 38 | I-5 | 0.5 | LiDFOB | 0.1 | 37.80% |
| Example 39 | I-5 | 0.5 | LiDFOB | 0.3 | 35.00% |
| Example 40 | I-5 | 0.5 | LiDFOB | 0.5 | 32.90% |
| Example 41 | I-5 | 0.5 | LiDFOB | 1 | 32.70% |
| Example 42 | I-11 | 0.5 | LiBF$_4$ | 0.2 | 32.30% |
| Example 43 | I-12 | 0.5 | LiBF$_4$ | 0.2 | 29.20% |
| Example 44 | I-30 | 0.5 | LiBF$_4$ | 0.2 | 30.70% |
| Example 45 | I-11 | 0.5 | LiDFOB | 0.5 | 31.50% |
| Example 46 | I-12 | 0.5 | LiDFOB | 0.5 | 29.00% |
| Example 47 | I-16 | 0.5 | LiDFOB | 0.5 | 26.90% |
| Example 48 | I-30 | 0.5 | LiDFOB | 0.5 | 29.70% |
| Comparative Example 3 | | | | | >50% |
| Comparative Example 4 | | | LiBF$_4$ | 0.2 | >50% |
| Comparative Example 5 | | | LiDFOB | 0.5 | >50% |

Note:
The blank space in Table 2 means that no addition of the corresponding additive.

It can be seen from Examples and Comparative Examples in Table 2 that when the additive C was added to the electrolyte containing the additive A, the high-temperature storage performance of the lithium-ion batteries was further improved at 4.5 V.

TABLE 3

| | Additive A | | Additive F | | Thickness swelling rate for floating charge at 45° C. |
|---|---|---|---|---|---|
| Example | Compound | Content (wt %) | Compound | Content (wt %) | |
| Example 3 | I-5 | 0.5 | | | 24.10% |
| Example 7 | I-11 | 0.5 | | | 20.50% |
| Example 8 | I-12 | 0.5 | | | 18.60% |
| Example 14 | I-30 | 0.5 | | | 26.80% |
| Example 49 | I-5 | 0.5 | DENE AND | 0.5 2 | 21.10% |
| Example 50 | I-5 | 0.5 | DENE AND | 0.5 3 | 19.50% |
| Example 51 | I-5 | 0.5 | DENE AND | 1 2 | 20.10% |
| Example 52 | I-5 | 0.5 | TCEP DENE AND | 0.5 1 2 | 16.70% |
| Example 53 | I-5 | 0.5 | TCEP DENE AND | 1 1 2 | 11.60% |
| Example 54 | I-5 | 0.5 | TCEP DENE AND | 1.5 1 2 | 9.80% |
| Example 55 | I-5 | 0.5 | HTCN DENE AND | 0.5 1 2 | 14.20% |
| Example 56 | I-5 | 0.5 | HTCN DENE AND | 1 1 2 | 10.20% |
| Example 57 | I-11 | 0.5 | DENE AND | 1 2 | 16.20% |
| Example 58 | I-12 | 0.5 | DENE AND | 1 2 | 14.50% |
| Example 59 | I-30 | 0.5 | DENE AND | 1 2 | 20.80% |
| Example 60 | I-11 | 0.5 | TCEP DENE AND | 0.5 1 2 | 13.60% |
| Example 61 | I-12 | 0.5 | TCEP DENE AND | 0.5 1 2 | 11.90% |
| Example 62 | I-30 | 1 | TCEP DENE AND | 0.5 1 2 | 19.20% |
| Comparative Example 6 | | | DENE AND | 1 2 | >50% |

Note:
The blank space in Table 3 means that no addition of the corresponding additive.

It can be seen from Examples and Comparative Examples in Table 3 that the combined use of the additive A and the additive F could significantly improve the floating charge performance of the lithium-ion batteries.

TABLE 4

| | Additive A | | Additive C | | Additive D | | Additive E | | Additive F | | Thickness swelling rate after storage for 24 h at 4.5 V and 85° C. |
|---|---|---|---|---|---|---|---|---|---|---|---|
| Example | Compound | Content (wt %) | Compound | Content (wt %) | Compound | Content (wt %) | Compound | Content (wt %) | Compound | Content (wt %) | |
| Example S1 | I-5 | 0.5 | LiBF$_4$ | 0.2 | | | V-6 V-12 | 4 0.5 | | | 30.60% |
| Example S2 | I-11 | 0.5 | LiBF$_4$ | 0.2 | | | V-6 V-12 | 4 0.5 | | | 28.90% |
| Example S3 | I-12 | 0.5 | LiDFOB | 0.5 | | | V-2 V-12 | 4 0.5 | | | 27.00% |
| Example S4 | I-16 | 0.5 | LiDFOB | 0.5 | | | V-2 V-12 | 4 0.5 | | | 22.30% |
| Example S5 | I-18 | 0.5 | | | | | V-2 V-12 | 4 0.5 | DENE AND | 1 2 | 20.10% |
| Example S6 | I-21 | 0.5 | | | | | V-2 V-12 | 4 0.5 | DENE AND | 1 2 | 24.70% |

TABLE 4-continued

| Example | Additive A Compound | Content (wt %) | Additive C Compound | Content (wt %) | Additive D Compound | Content (wt %) | Additive E Compound | Content (wt %) | Additive F Compound | Content (wt %) | Thickness swelling rate after storage for 24 h at 4.5 V and 85° C. |
|---|---|---|---|---|---|---|---|---|---|---|---|
| Example S7 | I-23 | 0.5 | | | | | V-6 | 4 | DENE | 1 | 25.70% |
| | | | | | | | V-15 | 0.5 | AND | 2 | |
| Example S8 | I-27 | 0.5 | | | | | V-6 | 4 | TCEP | 0.5 | 20.50% |
| | | | | | | | V-12 | 0.5 | DENE | 1 | |
| | | | | | | | | | AND | 2 | |
| Example S9 | I-30 | 0.5 | LiBF$_4$ | 0.2 | | | V-2 | 4 | TCEP | 0.5 | 22.90% |
| | | | | | | | V-12 | 0.5 | DENE | 1 | |
| | | | | | | | | | AND | 2 | |
| Example S10 | I-5 | 0.5 | | | LiPO$_2$F$_2$ | 0.3 | | | TCEP | 0.5 | 28.60% |
| | | | | | | | | | DENE | 1 | |
| | | | | | | | | | AND | 2 | |
| Example S11 | I-5 | 0.5 | | | LiPO$_2$F$_2$ | 0.3 | | | DENE | 1 | 31.50% |
| | | | | | | | | | AND | 2 | |
| Comparative Example S' | | | | | LiPO$_2$F$_2$ | 0.3 | | | DENE | 1 | 45.20% |
| | | | | | | | | | AND | 2 | |

Note:
The blank space in Table 4 means that no addition of the corresponding additive.

It can be seen from Examples and Comparative Examples in Table 4 that the combined use of the additive A and more of the additives C to F could further improve the high-temperature storage performance of the lithium-ion batteries.

In Examples 63 to 80 and Comparative Examples 7 to 9, the lithium-ion batteries were prepared according to the following method.

(1) Preparation of an Electrolyte

In an argon atmosphere glove box with a water content of less than 10 ppm, ethylene carbonate (EC for short), propylene carbonate (PC for short), and diethyl carbonate (DEC for short) were mixed uniformly at a mass ratio of 3:3:4 into a non-aqueous organic solvent, and a fully dried lithium salt LiPF$_6$ (1 M) was then dissolved in the non-aqueous organic solvent, to form a basic electrolyte. A specified amount of additive was added to the basic electrolyte to prepare the electrolyte in Examples 63 to 80 and Comparative Examples 7 to 9.

(2) Preparation of a Positive Electrode Plate

A positive electrode active substance NCM811 (whose molecular formula was LiNi$_{0.8}$Mn$_{0.1}$Co$_{0.1}$O$_2$), conductive carbon black, and a binder polyvinylidene fluoride (PVDF for short) were fully stirred and mixed at a weight ratio of 96:2:2 in an appropriate amount of N-methylpyrrolidone (NMP for short) solvent to form a uniform positive electrode slurry. The slurry was applied on a positive electrode current collector Al foil, and then dried and cold pressed to obtain a positive electrode plate.

(3) Preparation of a Negative Electrode Plate

A negative electrode active substance graphite, a binder styrene butadiene rubber (SBR for short), and a thickener sodium carboxymethyl cellulose (CMC for short) were fully stirred and mixed at a weight ratio of 97.4:1.4:1.2 in an appropriate amount of deionized water solvent to form a uniform negative electrode slurry. The slurry was applied on a negative electrode current collector Cu foil, and then dried and cold pressed to obtain a negative electrode plate.

(4) Preparation of a Separator

A PE porous polymer film was used as a separator.

(5) Preparation of a Lithium-Ion Battery

The prepared positive electrode plate, the separator, and the negative electrode plate were laminated in sequence, so that the separator was sandwiched between the positive electrode plate and the negative electrode plate to provide separation. Then the laminated product was wound to obtain an electrode assembly. The electrode assembly was placed in an outer package foil, leaving a liquid injection port. The prepared electrolyte was poured from the liquid injection port. Then, after vacuum packaging, standing, chemical conversion, shaping, and other processes, a lithium-ion battery was obtained.

Then, the following describes a test process of the high-temperature storage performance of the lithium-ion batteries at 85° C. in Examples 63 to 80 and Comparative Examples 7 to 9.

The battery was charged to 4.25 V at a constant current of 0.5 C at 25° C., and then charged to a current of 0.05 C at a constant voltage. A thickness of the lithium-ion battery was measured and recorded as d0. Then the lithium-ion battery was placed in an oven at 85° C. for 24 h, and the thickness of the lithium-ion battery at this time was measured and recorded as d. A thickness swelling rate (%) of the lithium-ion battery after high-temperature storage for 24 h was (d−d0)/d0×100%. If the thickness swelling rate exceeded 50%, the test was stopped.

Types and contents of the additives in the electrolyte and the performance test results of the lithium-ion batteries that are used in Examples 63 to 80 and Comparative Examples 7 to 9 are shown in Table 5. The content of each additive is a mass percentage calculated based on a mass of the electrolyte.

TABLE 5

| Example | Additive A Compound | Content (wt %) | Additive D Compound | Content (wt %) | Thickness swelling rate after storage for 24 h at 4.25 V and 85° C. |
|---|---|---|---|---|---|
| Example 63 | I-5 | 0.5 | | | 29.80% |
| Example 64 | I-5 | 0.5 | LiPO$_2$F$_2$ | 0.1 | 27.50% |
| Example 65 | I-5 | 0.5 | LiPO$_2$F$_2$ | 0.3 | 24.80% |
| Example 66 | I-5 | 0.5 | LiPO$_2$F$_2$ | 0.49 | 22.20% |
| Example 67 | I-5 | 0.5 | LiPO$_2$F$_2$ | 1 | 20.30% |
| Example 68 | I-5 | 0.5 | LiTFOP | 0.1 | 28.20% |

TABLE 5-continued

| | Additive A | | Additive D | | Thickness swelling rate after storage for 24 h at 4.25 V and 85° C. |
|---|---|---|---|---|---|
| Example | Compound | Content (wt %) | Compound | Content (wt %) | |
| Example 69 | I-5 | 0.5 | LiTFOP | 0.3 | 26.10% |
| Example 70 | I-5 | 0.5 | LiTFOP | 0.5 | 23.50% |
| Example 71 | I-5 | 0.5 | LiTFOP | 1 | 21.60% |
| Example 72 | I-11 | 0.5 | | | 27.90% |
| Example 73 | I-12 | 0.5 | | | 22.80% |
| Example 74 | I-30 | 0.5 | | | 28.50% |
| Example 75 | I-11 | 0.5 | $LiPO_2F_2$ | 0.3 | 22.30% |
| Example 76 | I-12 | 0.5 | $LiPO_2F_2$ | 0.3 | 17.00% |
| Example 77 | I-30 | 0.5 | $LiPO_2F_2$ | 0.3 | 22.50% |
| Example 78 | I-11 | 0.5 | LiTFOP | 0.5 | 21.70% |
| Example 79 | I-12 | 0.5 | LiTFOP | 0.5 | 16.20% |
| Example 80 | I-30 | 0.5 | LiTFOP | 0.5 | 22.00% |
| Comparative Example 7 | | | | | >50% |
| Comparative Example 8 | | | $LiPO_2F_2$ | 0.3 | 37.20% |
| Comparative Example 9 | | | LiTFOP | 0.5 | 39.30% |

Note:
The blank space in Table 5 means that no addition of the corresponding additive.

It can be seen from Examples and Comparative Examples in Table 5 that lithium difluorophosphate ($LiPO_2F_2$) and lithium tetrafluorooxalate phosphate (LiTFOP) could form a film at the cathode, which can inhibit the continuous oxidation and decomposition of the electrolyte and reduce gas production. Therefore, adding the additive D to the electrolyte containing the additive A can further improve the high-temperature storage performance.

In Examples 81 to 96 and Comparative Examples 10 to 12, the lithium-ion batteries were prepared according to the following method.

(1) Preparation of an Electrolyte

In an argon atmosphere glove box with a water content of less than 10 ppm, ethylene carbonate (EC for short), propylene carbonate (PC for short), diethyl carbonate (DEC for short), and ethyl propionate (EP for short) were mixed uniformly at a mass ratio of 1:2:6:1 into a non-aqueous organic solvent, and a fully dried lithium salt $LiPF_6$ (1 M) was then dissolved in the non-aqueous organic solvent, to form a basic electrolyte. A specified amount of additive was added to the basic electrolyte to prepare the electrolyte in Examples 81 to 96 and Comparative Examples 10 to 12.

(2) Preparation of a Positive Electrode Plate

A positive electrode active substance LCO (whose molecular formula was $LiCoO_2$), conductive carbon black, and a binder polyvinylidene fluoride (PVDF for short) were fully stirred and mixed at a weight ratio of 97.9:0.9:1.2 in an appropriate amount of N-methylpyrrolidone (NMP for short) solvent to form a uniform positive electrode slurry. The slurry was applied on a positive electrode current collector Al foil, and then dried and cold pressed to obtain a positive electrode plate.

(3) Preparation of a Negative Electrode Plate

A negative electrode active substance graphite, a silicon oxide material, a thickener sodium carboxymethyl cellulose (CMC for short), and modified polyacrylic acid were fully stirred and mixed at a weight ratio of 87:10:0.6:2.4 in an appropriate amount of deionized water solvent to form a uniform negative electrode slurry. The slurry was applied on a negative electrode current collector Cu foil, and then dried and cold pressed to obtain a negative electrode plate.

(4) Preparation of a Separator

A PE porous polymer film was used as a separator.

(5) Preparation of a Lithium-Ion Battery

The prepared positive electrode plate, the separator, and the negative electrode plate were laminated in sequence, so that the separator was sandwiched between the positive electrode plate and the negative electrode plate to provide separation. Then the laminated product was wound to obtain an electrode assembly. The electrode assembly was placed in an outer package foil, leaving a liquid injection port. The prepared electrolyte was poured from the liquid injection port. Then, after vacuum packaging, standing, chemical conversion, shaping, and other processes, a lithium-ion battery was obtained.

Then, the following describes a test process of the high-temperature storage performance of the lithium-ion batteries at 60° C. in Examples 81 to 96 and Comparative Examples 10 to 12.

The battery was charged to 4.45 V at a constant current of 0.5 C at 25° C., and then charged to a current of 0.05 C at a constant voltage. A thickness of the lithium-ion battery was measured and recorded as d0. Then the lithium-ion battery was placed in an oven at 60° C. for 12 days, the thickness of the lithium-ion battery at this time was measured and recorded as d, and the thickness was tested every 4 days. A thickness swelling rate (%) of the lithium-ion battery after storage at 60° C. for 12 days was (d−d0)/d0×100%. If the thickness swelling rate exceeded 100%, the test was stopped.

Types and contents of the additives in the electrolyte and the performance test results of the lithium-ion batteries that are used in Examples 81 to 96 and Comparative Examples 10 to 12 are shown in Table 6. The content of each additive is a mass percentage calculated based on a mass of the electrolyte.

TABLE 6

| | Additive A | | Additive B | | Thickness swelling rate after storage for 12 days at 4.45 V and 60° C. |
|---|---|---|---|---|---|
| Example | Compound | Content (wt %) | Compound | Content (wt %) | |
| Example 81 | I-5 | 0.5 | | | 57.80% |
| Example 82 | I-11 | 0.5 | | | 50.20% |
| Example 83 | I-12 | 0.5 | | | 45.30% |
| Example 84 | I-30 | 0.5 | | | 52.60% |
| Example 85 | I-5 | 0.5 | II-8 | 0.5 | 51.30% |
| Example 86 | I-5 | 0.5 | II-8 | 1 | 42.30% |
| Example 87 | I-5 | 0.5 | II-8 | 2 | 30.10% |
| Example 88 | I-5 | 0.5 | II-9 | 0.5 | 52.90% |
| Example 89 | I-5 | 0.5 | II-9 | 1 | 47.70% |
| Example 90 | I-5 | 0.5 | II-9 | 2 | 42.20% |
| Example 91 | I-11 | 0.5 | II-8 | 2 | 27.50% |
| Example 92 | I-12 | 0.5 | II-8 | 2 | 23.60% |
| Example 93 | I-30 | 0.5 | II-8 | 2 | 30.10% |
| Example 94 | I-11 | 0.5 | II-9 | 2 | 35.20% |
| Example 95 | I-12 | 0.5 | II-9 | 2 | 30.70% |
| Example 96 | I-30 | 0.5 | II-9 | 2 | 39.00% |
| Comparative Example 10 | | | | | >100% |
| Comparative Example 11 | | | II-8 | 1 | 80.30% |
| Comparative Example 12 | | | II-9 | 1 | >100% |

Note:
The blank space in Table 6 means that no addition of the corresponding additive.

It can be seen from Examples and Comparative Examples in Table 6 that when the compound II-8 or compound II-9 was in combined use with the additive A, the high-temperature storage performance of the lithium-ion batteries can be improved. A possible reason is that the compound II-8 or compound II-9 can form a film on the silicon negative electrode, and the additive A is used as a positive electrode protection additive, so that a synergistic effect of the additive A and the additive B improves the high-temperature storage performance of the lithium-ion batteries.

The above are merely embodiments of this application, and do not limit this application in any form. Although this application is disclosed as above with preferred embodiments, the embodiments are not intended to limit this application. Changes or modifications made by those skilled in the art using the technical content disclosed above without departing from the scope of the technical solution of this application are considered as equivalent embodiments and fall within the scope of the technical solution.

What is claimed is:

1. An electrolyte, comprising a compound represented by formula I-A;

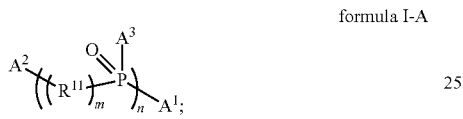

formula I-A wherein $A^1$, $A^2$, and $A^3$ are each independently selected from formula I-B or formula I-C, and at least two of $A^1$, $A^2$, and $A^3$ are formula I-C;

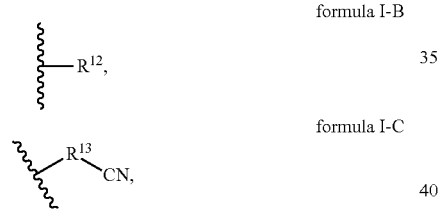

formula I-B formula I-C wherein in formula I-A, n is selected from integers 1 to 10, and m is 1;
wherein in formula I-B and formula I-C, ⁅− represents a site at which two adjacent atoms are joined;
wherein $R^{11}$ and $R^{13}$ are each independently selected from substituted or unsubstituted $C_2$-$C_{10}$ alkylene groups, substituted or unsubstituted $C_2$-$C_{10}$ alkenylene groups, substituted or unsubstituted $C_2$-$C_{10}$ alkynylene groups, substituted or unsubstituted $C_3$-$C_{10}$ allenylene groups, substituted or unsubstituted $C_6$-$C_{10}$ arylene groups, or substituted or unsubstituted $C_3$-$C_{10}$ alicyclic hydrocarbon groups, and when substituted, a substituent group comprises a halogen; and
$R^{12}$ is independently selected from halogens, substituted or unsubstituted $C_1$-$C_{10}$ alkyl groups, substituted or unsubstituted $C_2$-$C_{10}$ alkenyl groups, substituted or unsubstituted $C_2$-$C_{10}$ alkynyl groups, substituted or unsubstituted $C_3$-$C_{10}$ cumulative diene groups, substituted or unsubstituted $C_6$-$C_{10}$ aryl groups, or substituted or unsubstituted $C_3$-$C_{10}$ alicyclic hydrocarbon groups, and when substituted, a substituent group comprises a halogen,
wherein the electrolyte further comprises a multi-nitrile compound, wherein the multi-nitrile compound comprises at least one of 1,2,3-tris(2-cyanoethoxy)propane, 1,3,6-hexanetricarbonitrile, 1,2-bis(2-cyanoethoxy) ethane, or adiponitrile, and
wherein a ratio of a mass percentage of the compound represented by formula I-A to a mass percentage of the multi-nitrile compound is 0.01 to 1.

2. The electrolyte according to claim 1, wherein the compound represented by formula I-A comprises at least one of compounds represented by formula (I-1) to formula (I-30):

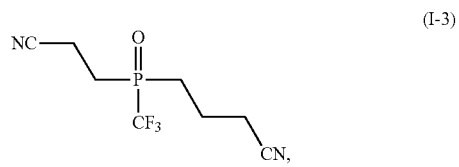

(I-3)

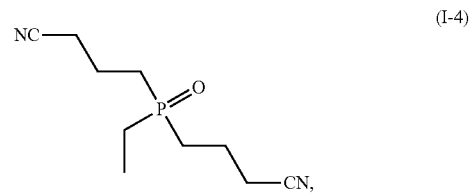

(I-4)

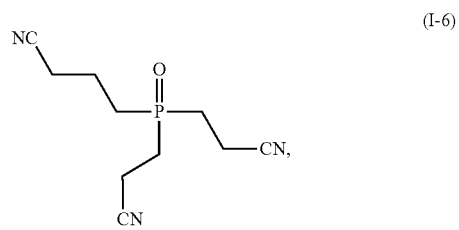

(I-6)

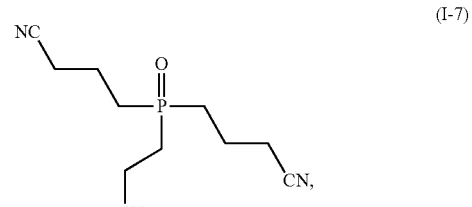

(I-7)

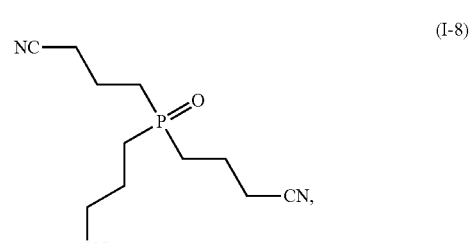

(I-8)

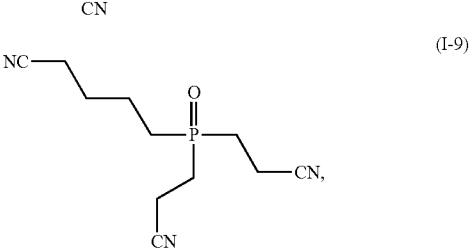

(I-9)

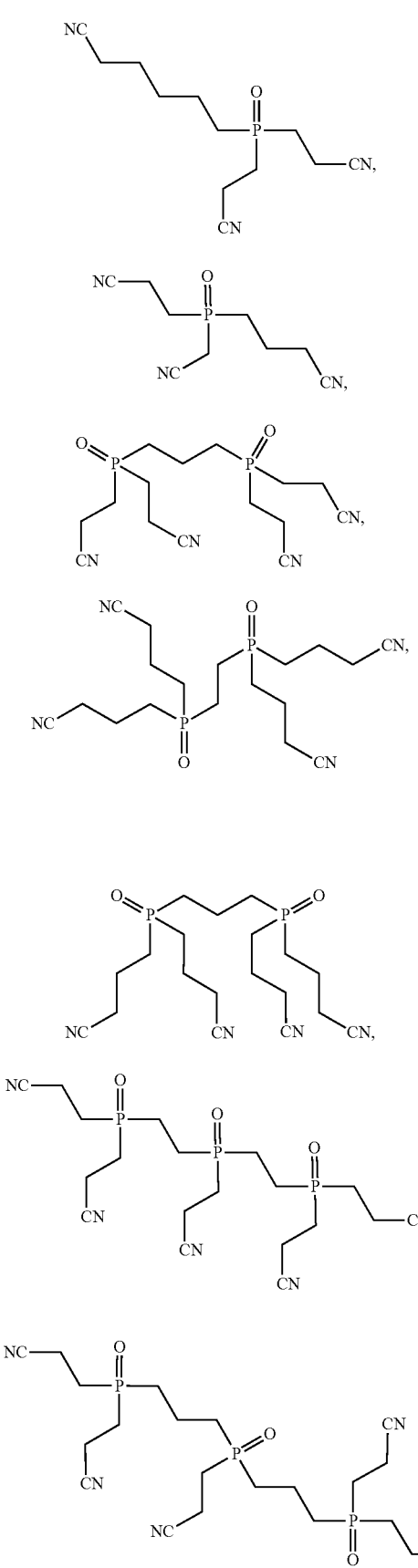
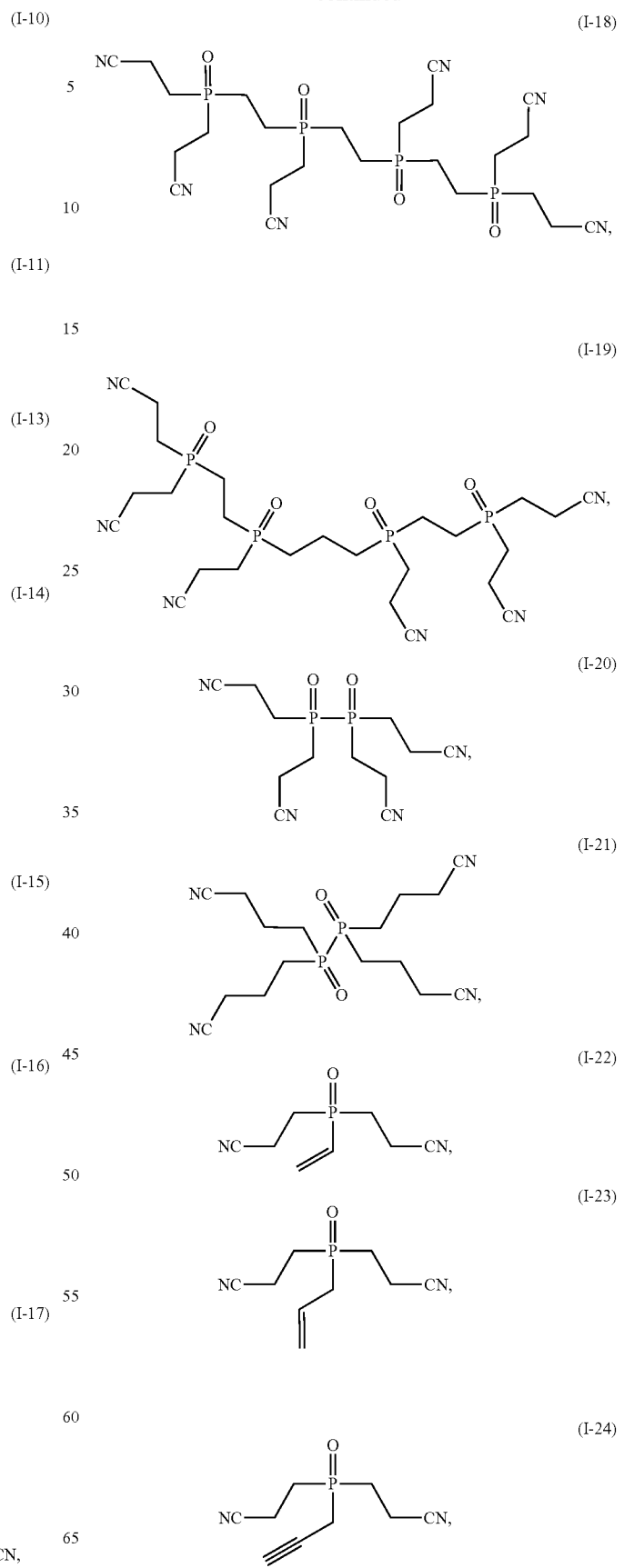

(Structural formulas I-25 through I-30 shown on the left column.)

3. The electrolyte according to claim 1, wherein the compound represented by formula I-A is 0.01% to 10% of the electrolyte by mass.

4. The electrolyte according to claim 1, further comprising at least one of a compound represented by formula II-A, a compound represented by formula III-A, a compound represented by formula IV-A, a compound represented by formula V-A, or a compound represented by formula V-B;

formula II-A: structure with $R^{21}$ and $R^{22}$ wherein $R^{21}$ and $R^{22}$ are each independently selected from substituted or unsubstituted $C_1$-$C_5$ alkyl groups, substituted or unsubstituted $C_2$-$C_5$ alkenyl groups, or substituted or unsubstituted $C_2$-$C_5$ alkynyl groups, and when substituted, a substituent group comprises a halogen; and $R^{21}$ and $R^{22}$ are capable of being bonded to form a cyclic structure;

formula III-A: $Li^+ [A^{34}\text{-}B(A^{31})(A^{32})(A^{33})]^-$ wherein $A^{31}$, $A^{32}$, $A^{33}$, and $A^{34}$ are each independently selected from one of halogens, formula III-X, formula III-Y, and formula III-Z, and when formula III-Y is selected, two or four of $A^{31}$, $A^{32}$, $A^{33}$, and $A^{34}$ are selected from formula III-Y to form a cyclic structure;

formula III-X: $-O-R^{31}$ formula III-Y: $-O-C(=O)-(R^{32})_k-$ formula III-Z: $-O-C(=O)-R^{33}$ wherein $R^{31}$ and $R^{33}$ are each independently selected from substituted or unsubstituted $C_1$-$C_6$ alkyl groups, or substituted or unsubstituted $C_2$-$C_6$ alkenyl groups;
$R^{32}$ is independently selected from substituted or unsubstituted $C_1$-$C_6$ alkylene groups, or substituted or unsubstituted $C_2$-$C_6$ alkenylene groups; and
when substituted, a substituent group comprises a halogen;
⊱— represents a site at which two adjacent atoms are joined;
in formula III-Y, an O atom is connected to a B atom in formula III-A, and k is 0 or 1;

formula IV-A: $Li^+ [A^{46}\text{-}P(A^{41})(A^{42})_x(A^{43})(A^{44})(A^{45})_y]^-$ wherein ⫶ represents a single bond or a double bond, and x and y each independently represent 0 or 1;

when one │ in formula IV-A represents a single bond, one of x and y is 1, and the other of x and y is 0;
when two │ in formula IV-A both represent a single bond, both x and y are 1;
when two │ in formula IV-A both represent a double bond, both x and y are 0;
$A^{42}$, $A^{43}$, $A^{45}$, and $A^{46}$ are each independently selected from halogens, substituted or unsubstituted $C_1$-$C_6$ alkyl groups, formula IV-B, formula IV-C, and formula IV-D; and when formula IV-C is selected, two or four of $A^{42}$, $A^{43}$, $A^{45}$, and $A^{46}$ are selected from formula IV-C to form a cyclic structure; $A^{41}$ and $A^{44}$ are each independently selected from oxygen, halogens, substituted or unsubstituted $C_1$-$C_6$ alkyl groups, formula IV-B, formula IV-C, or formula IV-D, and when formula IV-C is selected, $A^{41}$ and $A^{44}$ both are formula IV-C to form a cyclic structure; wherein when substituted, a substituent group comprises a halogen;
$A^{41}$, $A^{42}$, $A^{43}$, $A^4$, $A^{45}$, and $A^{46}$ are not all fluorine;

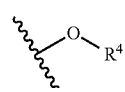

formula IV-B

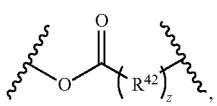

formula IV-C

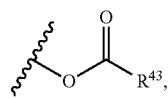

formula IV-D in formula IV-B, formula IV-C, and formula IV-D,
$R^{41}$ and $R^{43}$ are each independently selected from substituted or unsubstituted $C_1$-$C_6$ alkyl groups, or substituted or unsubstituted $C_2$-$C_6$ alkenyl groups; and
$R^{42}$ is selected from substituted or unsubstituted $C_1$-$C_6$ alkylene groups, or substituted or unsubstituted $C_2$-$C_6$ alkenylene groups;
wherein when substituted, a substituent group comprises a halogen;
in formula IV-C,
an O atom is connected to a P atom in formula IV-A, and z represents 0 or 1;

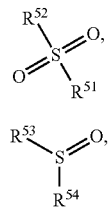

formula V-A formula V-B wherein $R^{51}$, $R^{52}$, $R^{53}$, and $R^{54}$ are each independently selected from substituted or unsubstituted $C_1$-$C_5$ alkyl groups, substituted or unsubstituted $C_2$-$C_{10}$ alkenyl groups, substituted or unsubstituted $C_2$-$C_{10}$ alkynyl groups, substituted or unsubstituted $C_3$-$C_{10}$ alicyclic groups, substituted or unsubstituted $C_6$-$C_{10}$ aryl groups, substituted or unsubstituted $C_1$-$C_6$ alicyclic heterocy-
clic groups, substituted or unsubstituted $C_1$-$C_6$ aromatic heterocyclic groups, or substituted or unsubstituted $C_1$-$C_6$ heteroatom-containing functional groups, wherein when substituted, a substituent group comprises a halogen; $R^{51}$ and $R^{52}$ are capable of being bonded to each other to form a cyclic structure; $R^{53}$ and $R^{54}$ are capable of being bonded to each other to form a cyclic structure; and a heteroatom in the heteroatom-containing functional group comprises at least one of B, N, O, Si, P, and S.

5. The electrolyte according to claim 4, wherein at least one of the following conditions are met: (a) the compound represented by formula II-A is 0.01% to 10% of the electrolyte by mass; (b) the compound represented by formula III-A is 0.1% to 5% of the electrolyte by mass; (c) the compound represented by formula IV-A is 0.1% to 5% of the electrolyte by mass; or (d) a sum of the compounds represented by formula V-A and formula V-B is 0.01% to 10% of the electrolyte by mass.

6. The electrolyte according to claim 4, wherein the compound represented by formula II-A comprises at least one of compounds represented by formula (II-1) to formula (II-22):

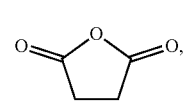
(II-1)

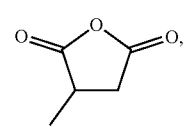
(II-2)

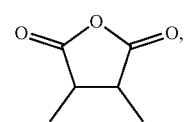
(II-3)

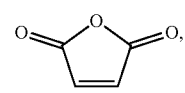
(II-4)

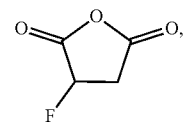
(II-5)

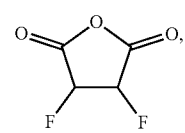
(II-6)

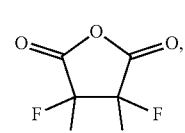
(II-7)

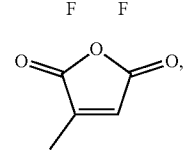
(II-8)

(II-9) 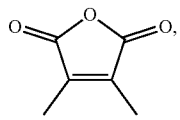

(II-10) 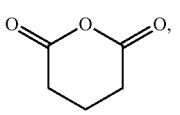

(II-11) 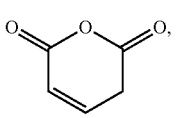

(II-12) 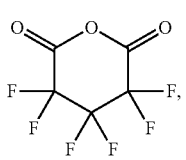

(II-13) 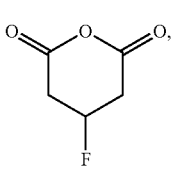

(II-14) 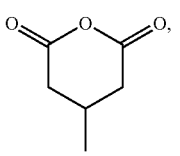

(II-15) 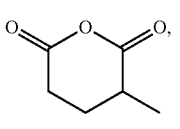

(II-16) 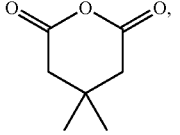

(II-17) 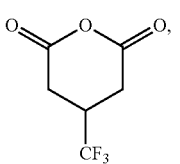

(II-18) 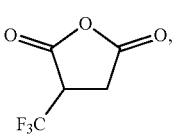

(II-19) 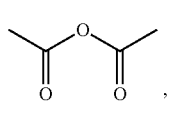

(II-20) 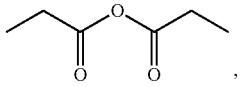

(II-21) 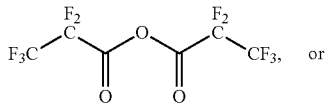

(II-22) 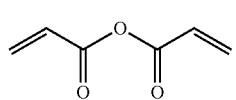

7. The electrolyte according to claim 4, wherein the compound represented by formula III-A comprises at least one of lithium tetrafluoroborate, lithium bis(oxalate)borate, or lithium difluoro(oxalato)borate.

8. The electrolyte according to claim 4, wherein the compound represented by formula IV-A comprises at least one of lithium difluorophosphate, lithium difluorobis(oxalato)phosphate, or lithium tetrafluoro(oxalato)phosphate.

9. The electrolyte according to claim 4, wherein the compound represented by formula V-A comprises at least one of compounds represented by formula (V-1) to formula (V-16):

(V-1) 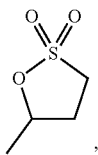

(V-2) 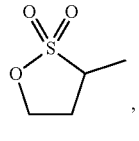

(V-3) 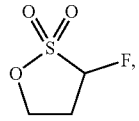

(V-4) 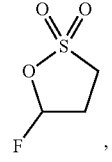

(V-5) 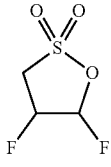

(V-6) 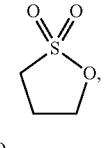

(V-7) 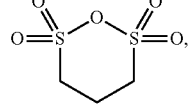

(V-8) 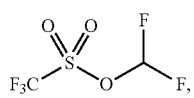

(V-9) 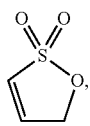

(V-10) 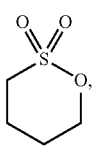

(V-11) 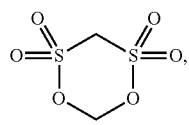

(V-12) 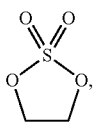

(V-13) 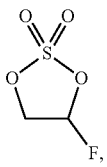

(V-14) 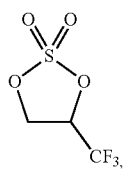

(V-15) 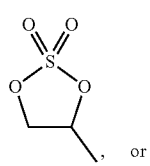, or (V-16) 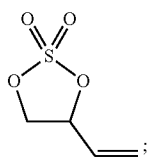;

and
the compound represented by formula V-B comprises at least one of compounds represented by formula (V-17) to formula (V-20):

(V-17) 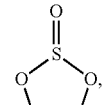

(V-18) 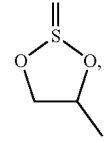

(V-19) 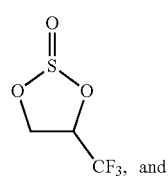, and (V-20) 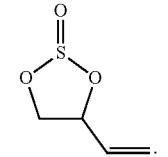.

10. An electrochemical device, comprising a positive electrode plate, a negative electrode plate, a separator, and an electrolyte, wherein the electrolyte comprising a compound represented by formula I-A;

formula I-A

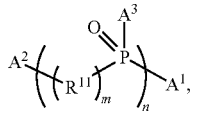

wherein $A^1$, $A^2$, and $A^3$ are each independently selected from formula I-B or formula I-C, and at least two of $A^1$, $A^2$, and $A^3$ are formula I-C;

formula I-B

formula I-C

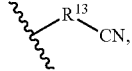

wherein in formula I-A, n is selected from integers 1 to 10, and m is 1;

wherein in formula I-B and formula I-C, ─┤ represents a site at which two adjacent atoms are joined;

wherein $R^{11}$ and $R^{13}$ are each independently selected from substituted or unsubstituted $C_2$-$C_{10}$ alkylene groups, substituted or unsubstituted $C_2$-$C_{10}$ alkenylene groups, substituted or unsubstituted $C_2$-$C_{10}$ alkynylene groups, substituted or unsubstituted $C_3$-$C_{10}$ allenylene groups, substituted or unsubstituted $C_6$-$C_{10}$ arylene groups, or substituted or unsubstituted $C_3$-$C_{10}$ alicyclic hydrocarbon groups, and when substituted, a substituent group comprises a halogen; and $R^{12}$ is independently selected from halogens, substituted or unsubstituted $C_1$-$C_{10}$ alkyl groups, substituted or unsubstituted $C_2$-$C_{10}$ alkenyl groups, substituted or unsubstituted $C_2$-$C_{10}$ alkynyl groups, substituted or unsubstituted $C_3$-$C_{10}$ cumulative diene groups, substituted or unsubstituted $C_6$-$C_{10}$ aryl groups, or substituted or unsubstituted $C_3$-$C_{10}$ alicyclic hydrocarbon groups, and when substituted, a substituent group comprises a halogen;

wherein the electrolyte further comprises a multi-nitrile compound, wherein the multi-nitrile compound comprises at least one of 1,2,3-tris(2-cyanoethoxy)propane, 1,3,6-hexanetricarbonitrile, 1,2-bis(2-cyanoethoxy)ethane, or adiponitrile, and wherein a ratio of a mass percentage of the compound represented by formula I-A to a mass percentage of the multi-nitrile compound is 0.01 to 1.

11. The electrochemical device according to claim 10, wherein the compound represented by formula I-A comprises at least one of compounds represented by formula (I-1) to formula (I-30):

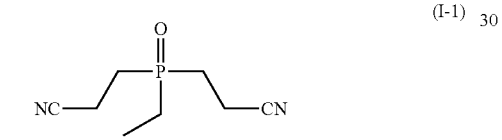
(I-1)

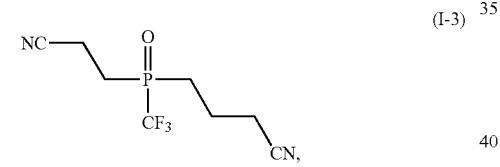
(I-3)

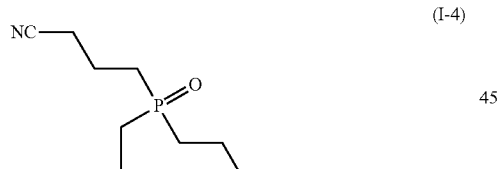
(I-4)

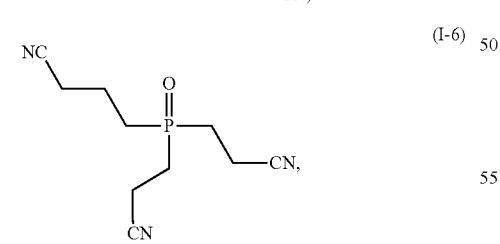
(I-6)

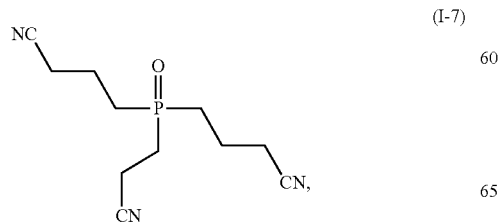
(I-7)

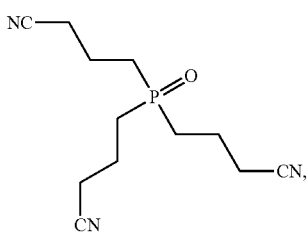
(I-8)

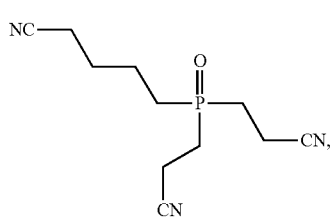
(I-9)

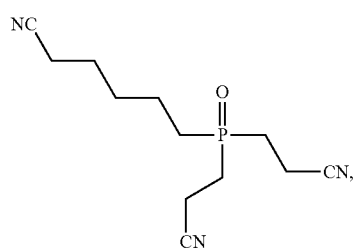
(I-10)

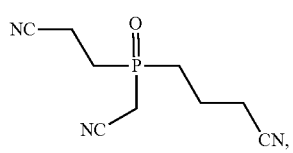
(I-11)

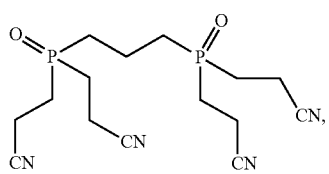
(I-13)

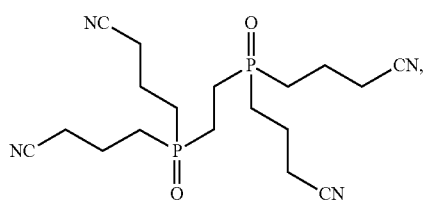
(I-14)

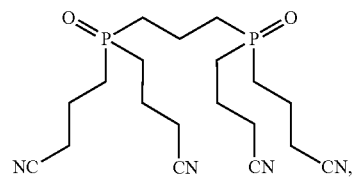
(I-15)

(I-16)
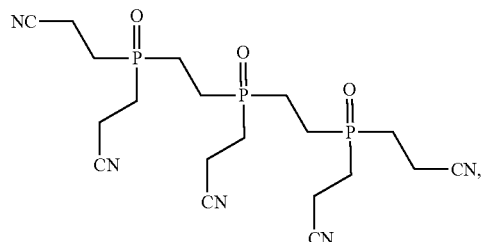
(I-17)
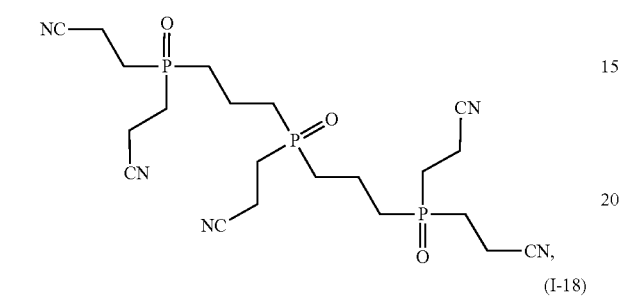
(I-18)
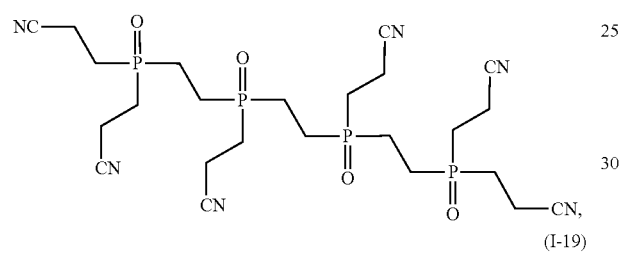
(I-19)
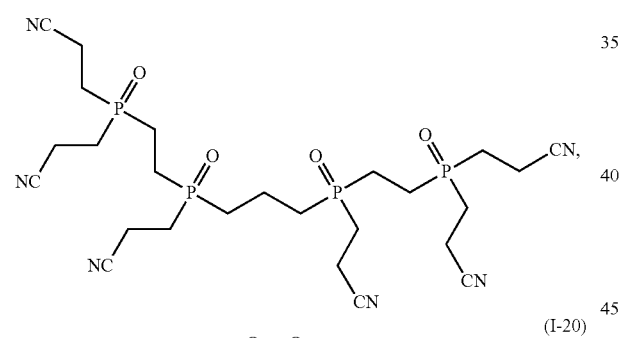
(I-20)
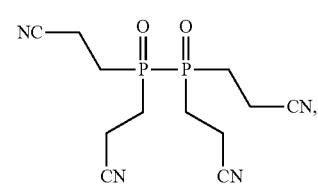
(I-21)
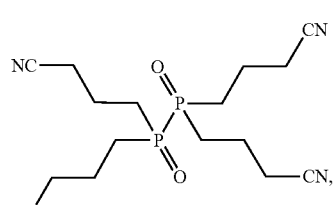
(I-22)
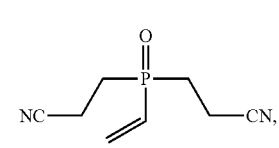
(I-23)
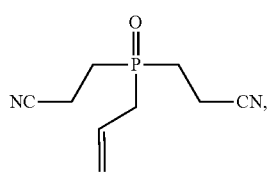
(I-24)
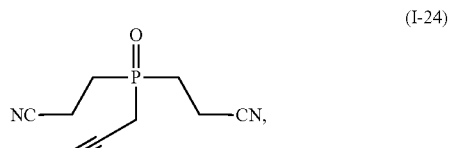
(I-25)
(I-26)
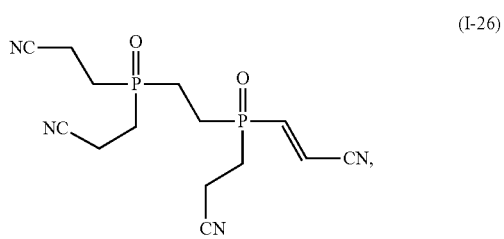
(I-27)
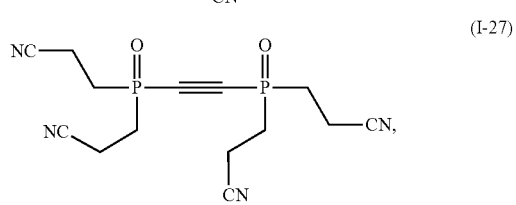
(I-28)
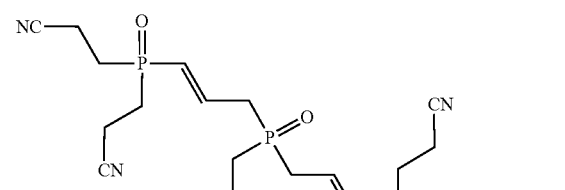
(I-29)
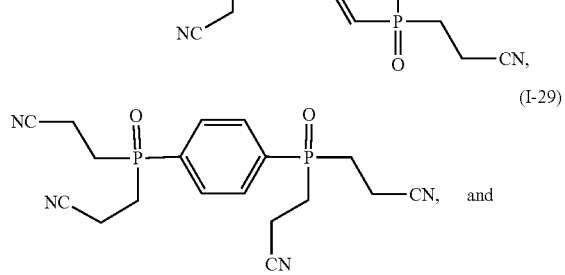
and

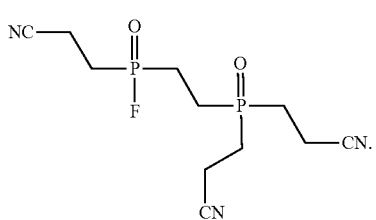

(I-30)

12. The electrochemical device according to claim 10, wherein the compound represented by formula I-A is 0.01% to 10% of the electrolyte by mass.

13. The electrochemical device according to claim 10, wherein the electrolyte further comprises at least one of a compound represented by formula II-A, a compound represented by formula III-A, a compound represented by formula IV-A, a compound represented by formula V-A, or a compound represented by formula V-B;

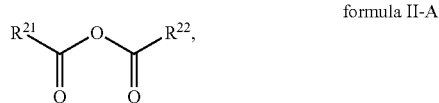

formula II-A wherein $R^{21}$ and $R^{22}$ are each independently selected from substituted or unsubstituted $C_1$-$C_5$ alkyl groups, substituted or unsubstituted $C_2$-$C_5$ alkenyl groups, or substituted or unsubstituted $C_2$-$C_5$ alkynyl groups, and when substituted, a substituent group comprises a halogen; and $R^{21}$ and $R^{22}$ are capable of being bonded to form a cyclic structure;

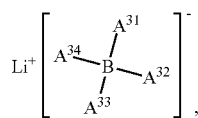

formula III-A wherein $A^{31}$, $A^{32}$, $A^{33}$, and $A^{34}$ are each independently selected from one of halogens, formula III-X, formula III-Y, and formula III-Z, and when formula III-Y is selected, two or four of $A^{31}$, $A^{32}$, $A^{33}$, and $A^{34}$ are selected from formula III-Y to form a cyclic structure;

formula III-X formula III-Y

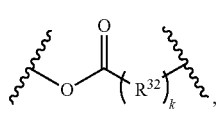

formula III-Z

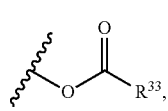

wherein $R^{31}$ and $R^{33}$ are each independently selected from substituted or unsubstituted $C_1$-$C_6$ alkyl groups, or substituted or unsubstituted $C_2$-$C_6$ alkenyl groups;

$R^{32}$ is independently selected from substituted or unsubstituted $C_1$-$C_6$ alkylene groups, or substituted or unsubstituted $C_2$-$C_6$ alkenylene groups; and when substituted, a substituent group comprises a halogen;

represents a site at which two adjacent atoms are joined;

in formula III-Y, an O atom is connected to a B atom in formula III-A, and k is 0 or 1;

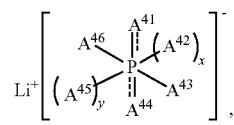

formula IV-A wherein ∣ represents a single bond or a double bond, and x and y each independently represent 0 or 1;

when one ∥ in formula IV-A represents a single bond, one of x and y is 1, and the other of x and y is 0;

when two ∣ in formula IV-A both represent a single bond, both x and y are 1;

when two ∣ in formula IV-A both represent a double bond, both x and y are 0;

$A^{42}$, $A^{43}$, $A^{45}$, and $A^{46}$ are each independently selected from halogens, substituted or unsubstituted $C_1$-$C_6$ alkyl groups, formula IV-B, formula IV-C, and formula IV-D, and when formula IV-C is selected, two or four of $A^{42}$, $A^{43}$, $A^{45}$, and $A^{46}$ are selected from formula IV-C to form a cyclic structure; $A^{41}$ and $A^{44}$ are each independently selected from oxygen, halogens, substituted or unsubstituted $C_1$-$C_6$ alkyl groups, formula IV-B, formula IV-C, or formula IV-D, and when formula IV-C is selected, $A^{41}$ and $A^{44}$ both are formula IV-C to form a cyclic structure; wherein when substituted, a substituent group comprises a halogen;

$A^{41}$, $A^{42}$, $A^{43}$, $A^{44}$, $A^{45}$, and $A^{46}$ are not all fluorine;

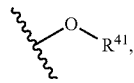

formula IV-B

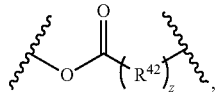

formula IV-C

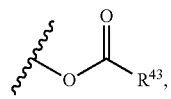

formula IV-D in formula IV-B, formula IV-C, and formula IV-D, $R^{41}$ and $R^{43}$ are each independently selected from substituted or unsubstituted $C_1$-$C_6$ alkyl groups, or substituted or unsubstituted $C_2$-$C_6$ alkenyl groups; and $R^{42}$ is selected from substituted or unsubstituted $C_1$-$C_6$ alkylene groups, or substituted or unsubstituted $C_2$-$C_6$ alkenylene groups;

wherein when substituted, a substituent group comprises a halogen;

in formula IV-C, an O atom is connected to a P atom in formula IV-A, and z represents 0 or 1;

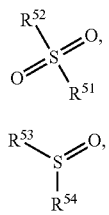

formula V-A formula V-B wherein $R^{51}$, $R^{52}$, $R^{53}$, and $R^{54}$ are each independently selected from substituted or unsubstituted $C_1$-$C_5$ alkyl groups, substituted or unsubstituted $C_2$-$C_{10}$ alkenyl groups, substituted or unsubstituted $C_2$-$C_{10}$ alkynyl groups, substituted or unsubstituted $C_3$-$C_{10}$ alicyclic groups, substituted or unsubstituted $C_6$-$C_{10}$ aryl groups, substituted or unsubstituted $C_1$-$C_6$ alicyclic heterocyclic groups, substituted or unsubstituted $C_1$-$C_6$ aromatic heterocyclic groups, or substituted or unsubstituted $C_1$-$C_6$ heteroatom-containing functional groups, wherein when substituted, a substituent group comprises a halogen; $R^{51}$ and $R^{52}$ are capable of being bonded to each other to form a cyclic structure; $R^{53}$ and $R^{54}$ are capable of being bonded to each other to form a cyclic structure; and a heteroatom in the heteroatom-containing functional group comprises at least one of B, N, O, Si, P, and S.

14. The electrochemical device according to claim 13, wherein at least one of the following conditions are met:

(a) the compound represented by formula II-A is 0.01% to 10% of the electrolyte by mass;

(b) the compound represented by formula III-A is 0.1% to 5% of the electrolyte by mass;

(c) the compound represented by formula IV-A is 0.1% to 5% of the electrolyte by mass; or (d) a sum of the compounds represented by formula V-A and formula V-B is 0.01% to 10% of the electrolyte by mass.

15. The electrochemical device according to claim 13, wherein the compound represented by formula II-A comprises at least one of compounds represented by formula (II-1) to formula (II-22):

(II-1)

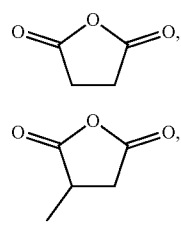

(II-2)

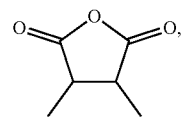

(II-3)

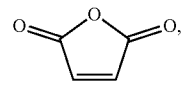

(II-4)

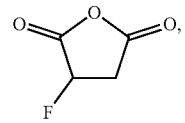

(II-5)

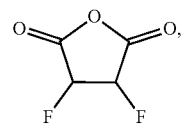

(II-6)

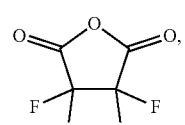

(II-7)

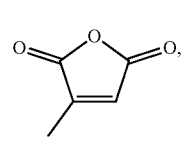

(II-8)

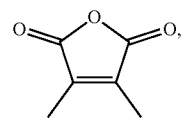

(II-9)

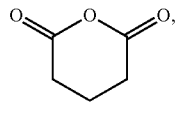

(II-10)

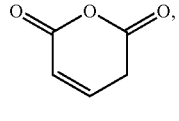

(II-11)

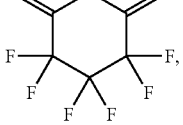

(II-12)

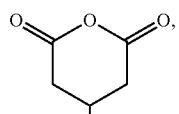

(II-13)

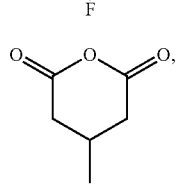

(II-14)

-continued

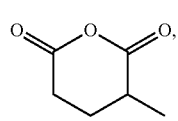 (II-15)

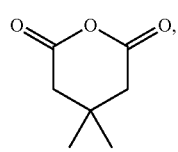 (II-16)

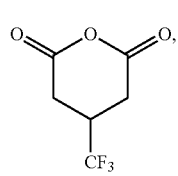 (II-17)

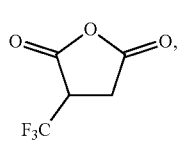 (II-18)

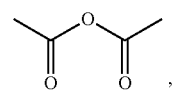 (II-19)

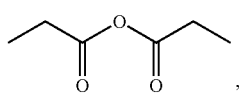 (II-20)

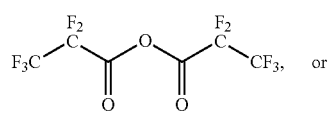 (II-21)

or

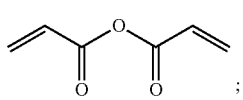 (II-22)

;

wherein the compound represented by formula III-A comprises at least one of lithium tetrafluoroborate, lithium bis(oxalate)borate, or lithium difluoro(oxalato)borate;

wherein the compound represented by formula IV-A comprises at least one of lithium difluorophosphate, lithium difluorobis(oxalato)phosphate, or lithium tetrafluoro(oxalato)phosphate;

wherein the compound represented by formula V-A comprises at least one of compounds

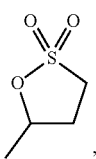 (V-1)

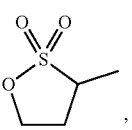 (V-2)

-continued

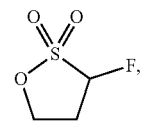 (V-3)

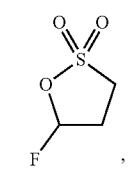 (V-4)

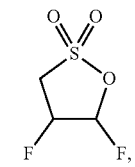 (V-5)

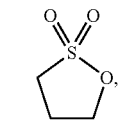 (V-6)

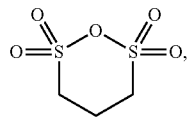 (V-7)

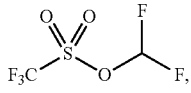 (V-8)

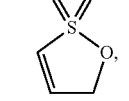 (V-9)

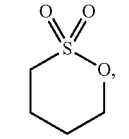 (V-10)

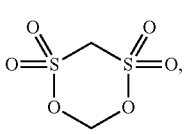 (V-11)

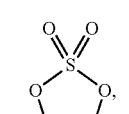 (V-12)

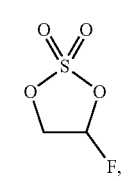 (V-13)

-continued

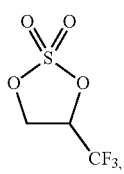
(V-14)

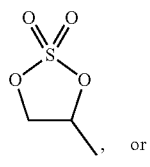
(V-15)

, or

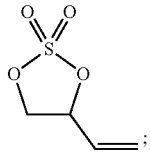
(V-16)

;

and
the compound represented by formula V-B comprises at least one of compounds represented by formula (V-17) to formula (V-20):

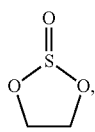
(V-17)

,

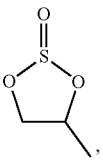
(V-18)

,

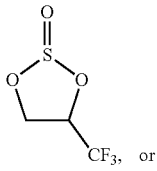
(V-19)

, or

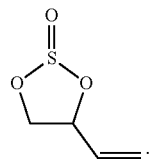
(V-20)

.

16. An electronic device, comprising an electrochemical device, the electrochemical device comprising a positive electrode plate, a negative electrode plate, a separator, and an electrolyte, wherein the electrolyte comprising a compound represented by formula I-A;

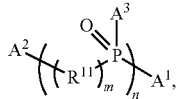
formula I-A wherein $A^1$, $A^2$, and $A^3$ are each independently selected from formula I-B or formula I-C, and at least two of $A^1$, $A^2$, and $A^3$ are formula I-C;

formula I-B

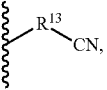
formula I-C wherein in formula I-A, n is selected from integers 1 to 10, and m is 1;
wherein in formula I-B and formula I-C, ⟞— represents a site at which two adjacent atoms are joined;
wherein $R^{11}$ and $R^{13}$ are each independently selected from substituted or unsubstituted $C_2$-$C_{10}$ alkylene groups, substituted or unsubstituted $C_2$-$C_{10}$ alkenylene groups, substituted or unsubstituted $C_2$-$C_{10}$ alkynylene groups, substituted or unsubstituted $C_3$-$C_{10}$ allenylene groups, substituted or unsubstituted $C_6$-$C_{10}$ arylene groups, or substituted or unsubstituted $C_3$-$C_{10}$ alicyclic hydrocarbon groups, and when substituted, a substituent group comprises a halogen; and
$R^{12}$ is independently selected from halogens, substituted or unsubstituted $C_1$-$C_{10}$ alkyl groups, substituted or unsubstituted $C_2$-$C_{10}$ alkenyl groups, substituted or unsubstituted $C_2$-$C_{10}$ alkynyl groups, substituted or unsubstituted $C_3$-$C_{10}$ cumulative diene groups, substituted or unsubstituted $C_6$-$C_{10}$ aryl groups, or substituted or unsubstituted $C_3$-$C_{10}$ alicyclic hydrocarbon groups, and when substituted, a substituent group comprises a halogen,
wherein the electrolyte further comprises a multi-nitrile compound, wherein the multi-nitrile compound comprises at least one of 1,2,3-tris(2-cyanoethoxy)propane, 1,3,6-hexanetricarbonitrile, 1,2-bis(2-cyanoethoxy)ethane, or adiponitrile, and
wherein a ratio of a mass percentage of the compound represented by formula I-A to a mass percentage of the multi-nitrile compound is 0.01 to 1.

* * * * *